United States Patent [19]
Auinbauh et al.

[11] Patent Number: 5,125,961
[45] Date of Patent: Jun. 30, 1992

[54] SUBSTITUTED PYRIDINE COMPOUNDS

[75] Inventors: Susan M. Auinbauh, St. Louis; Len F. Lee, St. Charles; Lisa L. McDermott, Sullivan, all of Mo.

[73] Assignee: Monsanto Company, St. Louis, Mo.

[21] Appl. No.: 743,652

[22] Filed: Aug. 12, 1991

[51] Int. Cl.$^5$ .................... C07D 413/04; A01N 43/40
[52] U.S. Cl. ........................................ 71/94; 546/275; 546/280
[58] Field of Search ..................... 546/275, 280; 71/94

[56] References Cited
U.S. PATENT DOCUMENTS
4,988,384  1/1991  Sing et al. .................... 546/278

Primary Examiner—Jane T. Fan
Attorney, Agent, or Firm—Grace L. Bonner; Howard C. Stanley

[57] ABSTRACT

Substituted pyridines characterized by having been substituted in the 3-position with an isoxazolyl or isothiazolyl radical. A method of using such pyridines as herbicides and herbicidal compositions containing such pyridines are described. Methods of preparing such substituted pyridines are also disclosed.

21 Claims, No Drawings

SUBSTITUTED PYRIDINE COMPOUNDS

This invention relates to a new class of substituted pyridinecarboxylic acid derivatives having a wide range of activity as herbicides.

Pyridine derivatives have, for many years, been investigated for use in biological sciences. For example, 2,6-bis(trifluoromethyl)-4-pyridinols have been found useful as herbicides and fungicides as disclosed in U.S. Pat. No. 3,748,334. Such compounds are characterized by substitution in the 4-position by a hydroxy radical. In addition to the hydroxy radical, the pyridine nucleus may also be substituted with bromo, chloro or iodo radicals. Trifluoromethyl pyridine derivatives have also been disclosed in U.S. Pat. Nos. 2,516,402 and 3,705,170 wherein the nucleus is further substituted by halogens as well as numerous other substituents. Some of these compounds are also noted to be useful as herbicides.

Also known because of their fungicidal activity are 4-substituted 2,6-dichloro-3,5-dicyanopyridines wherein the 4-position is substituted with alkyl, phenyl, naphthyl or pyridyl groups. Such compounds are disclosed in U.S. Pat. No. 3,284,293, while similar compounds are disclosed in U.S. Pat. No. 3,629,270 wherein the 4-position is substituted with a heterocyclic group wherein the hetero atom is oxygen or sulfur.

In EPO Patent 44,262 there are disclosed 2,6-dialkyl-3-phenylcarbamyl-5-pyridinecarboxylates and 5-cyano-compounds useful as herbicides. There is no disclosure of the 2-haloalkyl radicals or any substitution in the 4-position of the pyridine ring.

The pyridine derivatives have also received attention in the search for new herbicides and have been reported in U.S. Pat. Nos. 1,944,412, 3,637,716, and 3,651,070. All of these patents disclose polyhalo derivatives of dicarboxypyridines. All have in common the direct substitution on a ring carbon by a halogen in the 3- and 5-positions while the 2- and 6-positions are occupied by carboxylate groups. The 4-position is open to substitution by a wide range of materials including halogens, hydroxy radicals, alkoxy, and carboxyl groups. Such compounds have found utilization as herbicides, bactericides, and fungicides. When the 4-position is occupied by a silver salt, U.S. Pat. No. 1,944,412 discloses that such compounds have been utilized in the production of X-ray pictures with intravenous injection of such compounds.

Pyridinedicarboxylate compounds useful as herbicides are described in U.S. Pat. No. 4,692,184. These compounds have fluorinated methyl groups at the 2-and 6-positions and carboxylic acid derivative at the 3-and 5-positions.

Other pyridinedicarboxylate compounds including pyrazole amides are disclosed in U.S. Pat. No. 4,698,093. U.S. Pat. Nos. 4,066,438 and 4,180,395 disclose various herbicidal polyhalo substituted pyridyloxy compounds.

Other herbicidal pyridine compounds substituted at the 3- and/or 5-position with a carboxylic acid-derived heterocyclic moiety, as well as herbicidal compositions and use of these compounds are disclosed in U.S. Pat. No. 4,988,384.

BRIEF DESCRIPTION OF THE INVENTION

It is an object of this invention to provide herbicidal methods and compositions utilizing the novel pyridines of this invention.

The novel compounds of this invention are useful as herbicides or intermediates which can be converted to herbicides and are represented by the generic formula

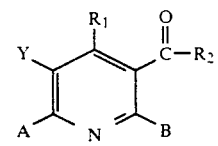

wherein:
A and B are independently selected from fluorinated methyl, chlorofluorinated methyl, and $C_1$–$C_4$ alkoxy, provided that at least one of A and B is trifluoromethyl;
$R_1$ is $C_1$–$C_7$ straight or branched alkyl, cyclopropylmethyl, or $C_3$–$C_6$ cycloalkyl;
$R_2$ is hydroxy, halo, $C_1$–$C_7$ straight or branched alkoxy, or $C_1$–$C_7$ straight or branched alkylthio; and
Y is a radical

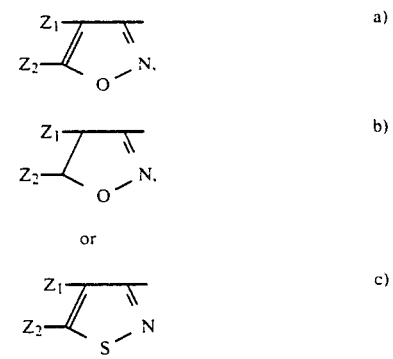

wherein:
$Z_1$ and $Z_2$ are independently selected from hydrogen, halo, cyano, phenylsulfonyl, $C_1$–$C_6$ straight or branched alkyl, $C_1$–$C_6$ straight or branched alkoxy, and $C_1$–$C_6$ straight or branched alkoxycarbonyl.

In the compounds, methods, and compositions of the present invention, it is preferred that Y be 3-isoxazolyl, more preferably 4-methyl-3-isoxazolyl.

As used herein, the term "halo" means chloro, bromo, fluoro, or iodo.

As used herein, the terms "fluorinated methyl" and "chlorofluorinated methyl" mean methyl radicals wherein one or more of the three hydrogen atoms have been replaced by a fluorine atom or a fluorine atom and a chlorine atom, respectively.

DETAILED DESCRIPTION OF THE INVENTION

The novel herbicidal compounds of this invention are readily prepared by reaction as illustrated in the following working examples. The present invention is merely illustrated by the following working examples but obviously is not limited thereto. All percentages are given on a weight/weight basis unless otherwise indicated.

The novel isoxazolyl-3-pyridinecarboxylic acid compounds (where Y is figure a) above) and 4,5-dihydroisoxazolyl-3-pyridinecarboxylic acid compounds (where Y is figure b) above) of the present invention can be synthesized via the cycloaddition of acetylenes or alkenes with a pyridyl nitrile oxide having the following structural formula

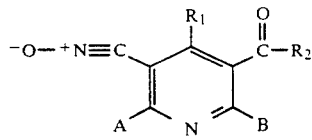

wherein $R_1$, $R_2$, A, and B are as defined above. This structure will for brevity be referred to as $PyrC\equiv N^+O^-$.

When this pyridine nitrile oxide is reacted with a suitably substituted olefin compound under cyclizing conditions, one obtains the dihydroisoxazoles of the present invention. When the pyridine nitrile oxide is reacted with a suitably substituted acetylene under cyclizing conditions, one obtains the isoxazoles of the present invention.

The isothiazolyl-3-pyridinecarboxylic acid compounds (where Y is figure c) above) of the present invention may be prepared from the isoxazoles by reduction under reducing conditions, followed by cyclization under cyclizing conditions, using methods well known to those skilled in the art. Alternatively, the isothiazoline derivatives may also be prepared and used in the methods of the present invention.

The pyridine nitrile oxide intermediates can be prepared by reacting a suitably substituted pyridine aldehyde with hydroxylamine under oxime-forming conditions to produce the oxime derivative which is then reacted under chlorinating conditions with N-chlorosuccinimide (NCS) to produce the chlorooxime derivative. Suitable pyridine aldehydes, such as 3-pyridinecarboxylic acid, 6-(difluoromethyl)-5-formyl-4-(2-methylpropyl)-2-(trifluoromethyl)-, methyl ester, and 3-pyridinecarboxylic acid, 2-(difluoromethyl)-5-formyl-4-(2-methylpropyl)-6-(trifluoromethyl)-, methyl ester, are disclosed in U.S. Pat. No. 4,988,384, incorporated herein by reference.

The resulting chlorooxime compound can be reacted with a strong organic base, such as triethylamine (TEA), to produce the desired pyridine nitrile oxide intermediate.

EXAMPLE A

This example illustrates the preparation of the oxime intermediate, 3-pyridinecarboxylic acid, 6-(difluoromethyl)-5-[(hydroxyimino)methyl]-4-(2-methylpropyl)-2-(trifluoromethyl)-, methyl ester.

3-Pyridinecarboxylic acid, 6-(difluoromethyl)-5-formyl-4-(2-methylpropyl)-2-(trifluoromethyl), methyl ester, (1.9 g, 0.0056 mol) was dissolved in 25 mL methanol. To this was added a solution of 0.47 g hydroxylamine hydrochloride (1.2 eq.) in 6 mL water, followed by 0.30 g NaOH (1.3 eq.) in 6 mL water. After 10 minutes, $^{19}$F-NMR showed two $CF_3$ peaks very close together. After 1.5 hour, there was no change in the fluorine spectrum, and TLC (10% ethyl acetate/cyclohexane) showed one spot. The product was a mixture of isomers. The methanol was removed by rotary evaporation. The residue was dissolved in ether and washed with water. The ether extracts were dried with anhydrous magnesium sulfate, filtered and concentrated in vacuo to an oil. This oil was purified by radial accelerated thin layer chromatography (50% methylene chloride/cyclohexane) which allowed for some separation of the regioisomers. There was recovered a 0.5 g sample of one isomer of the product and another 1.2 g sample of mixed isomers of the product. The total combined yield was 86%, and the melting point of the pure isomer was 73°-76° C.

EXAMPLE B

This example illustrates the preparation of the nitrile oxide intermediate, 3-pyridinecarboxylic acid, 5-cyano-6-(difluoromethyl)-4-(2-methylpropyl)-2-(trifluoromethyl)-, methyl ester N-oxide.

The oxime of Example A (2.39 g, 0.067 mol), 23 mL N,N-dimethylformamide (DMF) and 0.93 g N-chlorosuccinimide (NCS) were combined and heated to 65° C. After one-half hour $^{19}$F-NMR showed two peaks in the $CF_3$ region. Thereafter, 0.05 g NCS was added; and heating was resumed for 15 minutes. After cooling to room temperature, the reaction mixture was poured into water and extracted with ether. The ether phase was washed twice with more water. The ether phase was dried with anhydrous magnesium sulfate, filtered, and concentrated to a colorless oil (2.6 g, 0.0058 mol) which is the chlorooxime. It contained a small amount of ether. It was dissolved in 30 mL methylene chloride, and 0.08 mL triethylamine (1 eq.) was added. The reaction turned yellow. $^{19}$F-NMR showed the reaction was complete after 5 minutes. The reaction mixture was filtered through silica gel using methylene chloride and then concentrated in vacuo. The product was purified by radial accelerated thin layer chromatography (10% methylene chloride/cyclohexane) to give 1.3 g of product as a white solid (64% yield). m.p. 63°-65° C.

EXAMPLE C

This example illustrates the preparation of the oxime intermediate, 3-pyridinecarboxylic acid, 2-(difluoromethyl)-5-[(hydroxyimino)methyl]-4-(2-methylpropyl)-6-(trifluoromethyl)-, methyl ester.

3-Pyridinecarboxylic acid, 2-(difluoromethyl)-5-formyl-4-(2-methylpropyl)-6-(trifluoromethyl), methyl ester, (1.9 g, 0.0056 mol) was dissolved in 25 mL methanol. To this was added a solution of 0.47 g hydroxylamine hydrochloride (1.2 eq.) in 6 mL water, followed by 0.30 g NaOH (1.3 eq.) in 6 mL water. After 10 minutes, $^{19}$F-NMR showed two $CF_3$ peaks very close together. After 1.5 hour, there was no change in the fluorine spectrum, and TLC (10% ethyl acetate/cyclohexane) showed one spot. The product was a mixture of isomers. The methanol was removed by rotary evaporation. The residue was dissolved in ether and washed with water. The ether extracts were dried with anhydrous magnesium sulfate, filtered and concentrated in vacuo to an oil. This oil was purified by radial accelerated thin layer chromatography (50% methylene chloride/cyclohexane) which allowed for some separation of the regioisomers. There was recovered a 0.5 g sample of one isomer of the product and another 1.2 g sample of mixed isomers of the product. The total combined yield was 86%, and the melting point of the pure isomer was 73°-76° C.

Example D

This example illustrates the preparation of a nitrile oxide intermediate, 3-pyridinecarboxylic acid, 5-cyano-2-(difluoromethyl)-4-(2-methylpropyl)-6-(trifluoromethyl), methyl ester, N-oxide.

The oxime intermediate prepared in Example C, (4.33 g, 0.0122 mol), 50 mL DMF and 2.12 g NCS (1.3 eq.) were heated to 65° C. for 0.5 hour. $^{19}$F-NMR showed the reaction was complete. After cooling, it was poured into water and extracted with ether. The ether phase was washed several times with water and then dried with anhydrous magnesium sulfate, filtered, and concentrated in vacuo to give 4.4 g chlorooxime. This contained a small amount of ether. A 2.0 g portion of this material (0.005 mol) was dissolved in 45 mL tetrahydrofuran (THF) and 0.7 mL triethylamine (1 eq.) was added at room temperature. A white solid formed instantly. After 10 minutes, $^{19}$F-NMR showed the reaction was complete. It was filtered through silica gel using methylene chloride and concentrated in vacuo to a yellow oil. After purification by radial accelerated thin layer chromatography (20% methylene chloride/cyclohexane) 1.27 g of product was recovered as a white solid (72% yield). m.p. 46°–49° C.

EXAMPLE 1

4,5-Isoxazoledicarboxylic acid, 3-[6-(difluoromethyl)-5-(methoxycarbonyl)-4-(2-methylpropyl)-2-(trifluoromethyl)-3-pyridinyl]-, dimethyl ester.

A 2.4 g sample of the chlorooxime prepared as in the first step of Example D (0.0062 mol) was dissolved in 50 mL THF; and 0.9 mL triethylamine (1.1 eq.) was added at room temperature. A white solid formed. Then 1.0 mL dimethyl acetylenedicarboxylate (1.2 eq.) was added, and the reaction mixture was refluxed for 3 hours. $^{19}$F-NMR showed the reaction was complete. It was washed with water/NaCl and extracted with ether. The ether phase was dried with anhydrous magnesium sulfate, filtered, and concentrated in vacuo to 3.2 g orange oil. This was filtered through silica gel using methylene chloride and concentrated in vacuo to a yellow oil. After purification by radial accelerated thin layer chromatography (40% methylene chloride/cyclohexane) 2.0 g of Compound 1 were recovered as an oil (65% yield). $n_D^{25}$ 1.4803.

EXAMPLE 2

4,5-Isoxazoledicarboxylic acid, 3-[2-(difluoromethyl)-5-(methoxycarbonyl)-4-(2-methylpropyl)-6-(trifluoromethyl)-3-pyridinyl]-4,5-dihydro-, dimethyl ester.

The compound of Example A (2.05 g, 0.0058 mol), 25 mL DMF, and 0.90 g NCS were combined at room temperature. After 5 hours, $^{19}$F-NMR showed the reaction was complete. It was poured into water and extracted with ether. The ether phase was washed six times with water (about one liter was used) and then dried with anhydrous magnesium sulfate, filtered, and concentrated in vacuo to 2.2 g yellow oil. This was dissolved in 50 mL THF, and 0.8 mL triethylamine was added. A solid formed immediately. To this was added 0.8 mL (1.1 eq.) dimethyl maleate. The reaction stirred overnight at room temperature with very little reaction occurring. Another 0.8 mL dimethyl maleate was added; and the reaction was refluxed for 3.5 hours. At this time, $^{19}$F-NMR showed there was still some nitrile oxide present so 0.5 mL dimethyl maleate was added and reflux continued for another 1.5 hour. At this time, the reaction was complete. It was washed with water/NaCl and extracted with ether. The ether phase was dried with anhydrous magnesium sulfate, filtered, and concentrated in vacuo to 1.9 g dark oil. This was dissolved in methylene chloride and filtered through silica gel. After concentrating, 1.7 g yellow oil was recovered. It was purified by radial accelerated thin layer chromatography (40% methylene chloride/cyclohexane) and then recrystallized from hexanes to give 0.98 g of Compound 2 as a white solid (34% yield). mp 103°–105° C.

EXAMPLE 3

4,5-Isoxazoledicarboxylic acid, 3-[6-(difluoromethyl)-5-(methoxycarbonyl)-4-(2-methylpropyl)-2-(trifluoromethyl)-3-pyridinyl]-4,5-dihydro-, dimethyl ester.

The compound of Example C (1.92 g, 0.0054 mol), 20 mL DMF, and 0.86 g NCS (1 e.g.) were heated at 60°–70° C. for one hour. After cooling, the reaction was poured into water and extracted with ether. The ether phase was washed several times with more water. Then it was dried with anhydrous magnesium sulfate, filtered, and concentrated in vacuo to 2.16 g chlorooxime. This was dissolved in 50 mL THF and 0.8 mL triethylamine (1.1 e.g.) was added. A solid precipitated. Then 1.4 mL dimethyl maleate (2 eq.) was added and the reaction refluxed. After four hours, $^{19}$F-NMR showed the reaction was incomplete. Another 1 mL dimethyl maleate was added, and the reaction refluxed overnight. The reaction mixture was poured into water/NaCl and extracted with ether. The ether layer was dried with anhydrous magnesium sulfate, filtered, and concentrated in vacuo to an orange oil. This was heated on the Kugelrohr apparatus under reduced pressure at 40° C. to remove excess dimethyl maleate. The remaining material was filtered through silica gel using methylene chloride and then concentrated in vacuo to give a yellow liquid. This was further purified by radial accelerated thin layer chromatography (50% methylene chloride/cyclohexane) to give 1.5 g of Compound 3 as a pale yellow oil (56% yield). This gradually solidified, m.p. 77°–79° C.

EXAMPLE 4

3-Pyridinecarboxylic acid, 2-(difluoromethyl)-5-[4-(ethoxycarbonyl)-3-isoxazolyl]-4-(2-methylpropyl)-6-(trifluoromethyl)-, methyl ester.

The oxime compound of Example C, (2 13 g, 0.006 mol), 20 mL DMF and 0.92 g NCS (1.1 eq.) were heated at 80° C. for ½ hour. After cooling, the reaction was poured into water and extracted with ether. The ether phase was washed several times with more water (800 mL total). Then the reaction mixture was dried with anhydrous magnesium sulfate, filtered, and concentrated in vacuo to 2.4 g chlorooxime. This was dissolved in 50 mL THF and 0.9 mL triethylamine (1.1 eq.) was added. A white solid precipitated. Then 2.15 g pyrrolidine enamine of ethyl propiolate (2 eq.) was added and the reaction was refluxed. After 0.5 hours $^{19}$F-NMR showed two CF$_3$ peaks at ~3:2 ratio. There was no change after another two hours reflux. After cooling, it was poured into water/NaCl and extracted with ether. The ether phase was dried with anhydrous magnesium sulfate, filtered, and concentrated in vacuo to 3.7 g yellow, oily solid. $^{19}$F-NMR and TLC (30% ethyl acetate/cyclohexane) showed two products were formed. The crude material was treated with hexanes. A yellowish solid separated from solution and was collected by filtration. The hexanes solution was concentrated in vacuo and filtered through silica gel using methylene chloride. The methylene chloride phase was concentrated in vacuo to give 1.25 g of Compound 4 as a pale yellow oil (46% yield). $n_D^{25}$ 1.4726.

EXAMPLE 5

3-Pyridinecarboxylic acid, 2-(difluoromethyl)-5-[4,5-dihydro-5-(methoxycarbonyl)-3-isoxazolyl]-4-(2-methylpropyl)-6-(trifluoromethyl)-, methyl ester.

The compound of Example C (1.6 g, 0.0045 mol), 20 mL DMF and 0.74 g NCS (1.2 eq.) were heated at 50°-80° C. for 40 minutes. After cooling, the reaction was poured into water and extracted with ether. The ether phase was washed several times with more water (800 mL total). Then it was dried with anhydrous magnesium sulfate, filtered, and concentrated in vacuo to 1.7 g chlorooxime. This was dissolved in 50 mL THF, and 0.7 mL triethylamine was added. A white solid precipitated. Then 0.5 mL methyl acrylate (1.2 eq.) was added and the reaction was stirred at room temperature. After 3.5 hours, $^{19}$F-NMR showed both nitrile oxide and product were present. Another 0.2 mL methyl acrylate was added. The reaction mixture was stirred overnight. It was poured into water/NaCl and extracted with ether. The ether layer was dried with anhydrous magnesium sulfate, filtered and concentrated in vacuo to 1.76 g yellow oil. This was purified by radial accelerated thin layer chromatography (30% methylene chloride/cyclohexane) to give 1.36 g of Compound 5 as a white solid (70% yield). m.p. 93°-95° C.

EXAMPLE 6

3-Pyridinecarboxylic acid, 6-(difluoromethyl)-5-(3-isoxazolyl)-4-(2-methylpropyl)-2-(trifluoromethyl)-, methyl ester.

The compound of Example A (2.87 g, 0.0081 mol), 25 mL DMF and 1.46 g NCS (1.3 eq.) were combined and stirred at room temperature overnight. The reaction was poured into water and extracted with ether. The ether phase was washed several times with water (900 mL total). The ether phase was dried with anhydrous magnesium sulfate, filtered, and concentrated in vacuo to 3.4 g chlorooxime. This was dissolved in 50 mL toluene, followed by 2.5 mL triethylamine (2.2 eq.). A white solid precipitated. Phenyl vinyl sulfoxide (1.6 mL, 1.5 eq.) was added, and the reaction was refluxed for 1.5 hour. $^{19}$F-NMR indicated the reaction was complete. After cooling, it was poured into water/NaCl and extracted with ether. The ether phase was dried with anhydrous magnesium sulfate, filtered, and concentrated in vacuo to 4 g orange oil. This was filtered through silica gel using 50% methylene chloride/cyclohexane, followed by 100% methylene chloride. By concentrating the fractions, 3 g orange oil was recovered. This was purified by multiple radial accelerated thin layer chromatography runs (5% ethyl acetate/cyclohexane) and recrystallizations from hexanes. Compound 6 was recovered as 1 g off-white solid (33% yield). m.p. 76°-81° C.

EXAMPLE 7

3-Pyridinecarboxylic acid, 2-(difluoromethyl)-5-(4,5-dihydro-3-isoxazolyl)-4-(2-methylpropyl)-6-(trifluoromethyl)-, methyl ester.

The oxime compound of Example C (1.94 g, 0.0055 mol), 20 mL DMF and 1.0 g NCS (1.3 eq.) were heated to 90° C., and then the reaction slowly cooled to room temperature over the next hour. The reaction was poured into water and extracted with ether. The ether phase was washed several times with water (1000 mL total). Then it was dried with anhydrous magnesium sulfate, filtered and concentrated in vacuo to isolate the chlorooxime. This was dissolved in 50 mL THF, followed by 0.9 mL triethylamine (1.2 eq.). A white solid precipitated. After one hour, this reaction was filtered through celite, and the pad was washed with THF. The filtrate was concentrated in vacuo to a yellow oil. This was placed in a 60 mL stainless steel reactor along with 30 mL THF. The reactor was pressurized with ethylene at 100 psi (689 kiloPascals). After 2 hours, $^{19}$F-NMR indicated the reaction was nearly complete. The reactor was kept at 100 psi ethylene overnight. The reactor contents were concentrated in vacuo to 2.0 g yellow oil. This was purified by radial accelerated thin layer chromatography (20% methylene chloride/cyclohexane) to give 1.28 g of Compound 7 as a white solid (61% yield). m.p. 65°-69° C.

EXAMPLE 8

3-Pyridinecarboxylic acid, 2-(difluoromethyl)-5-[5-(methoxycarbonyl)-3-isoxazolyl]-4-(2-methylpropyl)-6-(trifluoromethyl)-, methyl ester.

The oxime compound of Example C (3.5 g, 0.01 mol), 30 mL DMF and 1.8 g NCS (1 3 eq.) were combined at room temperature. After six days, the reaction was poured into water and extracted with ether. The ether phase was washed several times with water (900 mL total). The ether phase was dried with anhydrous magnesium sulfate, filtered, and concentrated in vacuo to 3.9 g chlorooxime. Some of this chlorooxime (1.92 g, 0.0049 mol) was dissolved in 50 mL THF, and then 0.9 mL triethylamine was added to it. A white solid precipitated. Methyl propiolate (0.5 mL, 1.2 eq.) was added, and the reaction was refluxed. After 2 hours, $^{19}$F-NMR indicated the reaction was complete. It was poured into water/NaCl and extracted with ether. The ether phase was dried with anhydrous magnesium sulfate, filtered, and concentrated in vacuo to 2.1 g brown oil. $^{1}$H-NMR and $^{19}$F-NMR showed two products were formed in a ratio of ~3:1. The crude product was filtered through silica gel using 50% methylene chloride/cyclohexane. The filtrate was concentrated in vacuo to 1.9 g colorless oil which gradually solidified. This was recrystallized from hexanes to give exclusively Compound 8 as 0.70 g white solid (33% yield). mp 107°-109° C.

EXAMPLE 9

3-Pyridinecarboxylic acid, 2-(difluoromethyl)-5-(3-isoxazolyl)-4-(2-methylpropyl)-6-(trifluoromethyl)-, methyl ester.

The oxime compound of Example C (2.21 g; 0.0062 mol), 25 mL DMF and 1.08 g NCS (1.2 eq.) were combined and heated to 95° C. Over the next hour, the reaction was allowed to cool to room temperature. It was poured into water and extracted with ether. The ether phase was washed several times with water (900 mL total). Then the reaction mixture was dried with anhydrous magnesium sulfate, filtered, and concentrated in vacuo to the chlorooxime. This material was dissolved in 50 mL toluene, followed by 1.0 mL triethylamine (1.2 eq.) and 0.9 mL phenyl vinyl sulfoxide (1.1 eq.). A white solid precipitated. The reaction was refluxed for 2.5 hours. After cooling, it was poured into water/NaCl and extracted with ether. The ether phase was dried with anhydrous magnesium sulfate, filtered, and concentrated in vacuo to 3 g orange oil. This was filtered through silica gel using cyclohexane first, followed by 50% methylene chloride/cyclohexane, and then 100% methylene chloride. Fractions were collected and analyzed by TLC. One fraction yielded 0.9 g impure product which after recrystallization from hexanes gave 0.7 g pure product. Another fraction yielded 1.2 g impure product which was then further purified by radial accelerated thin layer chromatography (5% ethyl acetate/cyclohexane). After multiple chromatography runs and recrystallizations a total of 1.4 g of Compound 9 was recovered as a white solid (60% yield). m.p. 94°–96° C.

EXAMPLE 10

3-Pyridinecarboxylic acid, 2-(difluoromethyl)-5-[4-(methoxycarbonyl)-3-isoxazolyl]-4-(4-(2-methylpropyl)-6-(trifluoromethyl)-, methyl ester.

The oxime compound of Example C (5.0 g, 0.0141 mol), 40 mL DMF and 2.54 g NCS (1.4 eq.) were heated together to 80° C. Heating was stopped and the reaction cooled to 50° C. The reaction was poured into water and extracted with ether. The ether phase was washed several times with water (1000 mL total) and then dried with anhydrous magnesium sulfate, filtered, and concentrated in vacuo to 5.48 g chlorooxime.

Methyl propiolate (2 mL, 0.022 mol) was dissolved in 20 mL THF and cooled in a water bath before adding 2 mL pyrrolidine (1.1 eq.) by pipette. After two hours, the reaction was concentrated in vacuo to 3.5 g yellow solid. This was recrystallized from hexanes to give 2.6 g pyrrolidine enamine of methyl propiolate as white needles.

The chlorooxime (2.73 g, 0.007 mol), 50 mL THF and 1.29 g of the enamine (1.1 eq.) were combined at room temperature. After one hour, $^{19}$F-NMR showed no reaction had occurred. So the solution was refluxed for two hours. During this time, the reaction turned yellow and a solid formed (pyrrolidine hydrochloride). After cooling, it was poured into water/NaCl and extracted with ether. The ether phase was dried with anhydrous magnesium sulfate, filtered, and concentrated in vacuo to 3.2 g yellow oil. This was filtered through silica gel using 50% methylene chloride/cyclohexane. After concentrating in vacuo, 2.66 g of Compound 10 was recovered as a white solid (87% yield). m.p. 70°–73° C.

EXAMPLE 11

3-Pyridinecarboxylic acid, 2-(difluoromethyl)-5-[5-(ethoxycarbonyl)-3-isoxazolyl]-4-(2-methylpropyl)-6-(trifluoromethyl)-, methyl ester.

The chlorooxime prepared as in Example 8 (1.88 g, 0.0048 mol) was dissolved in 50 mL THF, and 1 mL triethylamine (1.5 eq.) was added to it. A white solid precipitated. Then ethyl propiolate (0.6 mL, 1.2 eq.) was added to the solution and refluxed. After two hours, $^{19}$F-NMR indicated the reaction was complete, resulting in two products (Compound 11 and Compound 4). The reaction was cooled and poured into water/NaCl and extracted with ether. The ether phase was dried with anhydrous magnesium sulfate, filtered, and concentrated in vacuo to 2 g brown oil. This was filtered through silica gel using 50% methylene chloride/cyclohexane. The filtrate was concentrated in vacuo to 2 g colorless oil which gradually solidified. This was recrystallized from hexanes to give 0.09 g of Compound 11 as fine, white crystals (33% yield). m.p. 82°–83° C.

EXAMPLE 12

3-Pyridinecarboxylic acid, 2-(difluoromethyl)-5-[5-(ethoxycarbonyl)-4,5-dihydro-3-isoxazolyl]-4-(2-methylpropyl)-6-(trifluoromethyl)-, methyl ester.

The chlorooxime prepared in Example 10 (2.75 g, 0.0071 mol) was dissolved in 50 mL THF, followed by 1.2 mL triethylamine (1.2 eq.). A white solid precipitated. Ethyl acrylate (0.95 mL, 1.2 eq.) was added, and the reaction was refluxed. After 0.5 hour, $^{19}$F-NMR showed the reaction was complete. After cooling, it was poured into water/NaCl and extracted with ether. The ether phase was dried with anhydrous magnesium sulfate, filtered, and concentrated in vacuo to 3 g yellow oil. This was purified by radial accelerated thin layer chromatography (30% methylene chloride/cyclohexane) to give 2.32 g of Compound 12 as an oil which gradually solidified (72% yield). m.p. 72°–74° C.

EXAMPLE 13

3-Pyridinecarboxylic acid, 2-(difluoromethyl)-5-(4,5-dihydro-5-methoxy-3-isoxazolyl)-4-(2-methylpropyl)-6-(trifluoromethyl)-, methyl ester.

The compound of Example D (2.47 g, 0.007 mol) and 20 mL THF were placed in a 60 mL stainless steel reactor. This was charged with methyl vinyl ether at 13 psi (8.3 kiloPascals). The reaction mixture sat overnight at room temperature. In the morning, $^{19}$F-NMR showed the reaction was complete. It was concentrated in vacuo to a yellow oil. This was filtered through silica gel using methylene chloride and then purified by radial accelerated thin layer chromatography (30% methylene chloride/cyclohexane). Compound 13 was recovered as 1.7 g pale yellow oil which gradually solidified (59% yield). m.p. 93°–95° C.

EXAMPLE 14

3-Pyridinecarboxylic acid, 2-(difluoromethyl)-5-(4,5-dihydro-5-methyl-3-isoxazolyl)-4-(2-methylpropyl)-6-(trifluoromethyl)-, methyl ester.

The compound of Example D (5.03 g, 0.0143 mol) and 25 mL THF were charged to a 60 mL stainless steel reactor. The reactor was pressurized with propene at a maximum of 100 psi at room temperature. After 1.5 hour, $^{19}$F-NMR showed the reaction was complete. The reactor was vented and the contents concentrated in vacuo to a 5.4 g yellow solid. This was filtered through silica gel using methylene chloride, and the filtrate was concentrated in vacuo to a yellow solid. This was recrystallized from hexanes to give 3.06 g of product as a white solid. The filtrate was concentrated in vacuo to 2 g yellow oil. This was further purified by radial accelerated thin layer chromatography (30% methylene chloride/cyclohexane) to give 0.064 g of Compound 14. A total of 3.7 g of Compound 14 was recovered (66% yield). m.p. 86°–88° C.

EXAMPLE 15

3-Pyridinecarboxylic acid, 2-(difluoromethyl)-5-(5-ethoxy-4,5-dihydro-3-isoxazolyl)-4-(2-methylpropyl)-6-(trifluoromethyl)-, methyl ester.

The compound of Example D (2.55 g, 0.0072 mol), 30 mL THF and 1 mL ethyl vinyl ether (!.5 eq.) were combined at room temperature in a 60 mL stainless steel reactor. After two hours, $^{19}$F-NMR showed the reaction was complete. The reactor contents were concentrated in vacuo to 2.8 g yellow oil. This was filtered through silica gel using methylene chloride and the filtrate concentrated to 2.6 g yellow oil. This was purified by radial accelerated thin layer chromatography (30% methylene chloride/cyclohexane) to give 1.18 g of Compound 15 as an oil (38% yield). $n_D^{25}$ 1.4687.

EXAMPLE 16

3-Pyridinecarboxylic acid, 2-(difluoromethyl)-5-(5-methyl-3-isoxazolyl)-4-(2-methylpropyl)-6-(trifluoromethyl)-, methyl ester.

The oxime compound of Example C (4.2 g, 0.012 mol), 35 mL DMF, and 2.0 g NCS (1.2 eq.) were heated together to 75° C. Then heating was stopped, and the reaction cooled to 50° C. over the next one-half hour. The reaction was poured into water (1000 mL total) and then dried with anhydrous magnesium sulfate, filtered, and concentrated in vacuo to 4.5 g chlorooxime which contained some residual ether. This was dissolved in 110 mL THF, followed by 1.5 mL (1.3 eq.) 2-bromopropene and 3.3 mol triethylamine (2 eq.). A white solid formed immediately. The reaction was refluxed for 1 hour, and then the reaction mixture was allowed to stand overnight at room temperature. In the morning, $^{19}$F-NMR indicated only a small amount of reaction. The reaction mixture was filtered and concentrated in vacuo to a yellow oil. This was charged to a stainless steel 60 mL reactor along with 22 mL THF, 2 mL triethylamine and 1.5 mL 2-bromopropene. The reactor was closed and heated by an oil bath at 70°-80° C. After two hours, $^{19}$F-NMR showed starting material and two products. There was observed a white solid in the reactor which was probably triethylamine hydrobromide. Another 1 mL 2-bromopropene was added and heating resumed. After another 1.5 hour, $^{19}$F-NMR showed the reaction was still incomplete so 0.5 mL 2-bromopropene was added and heating continued for 1.5 hour. The reaction mixture was cooled, and it sat over the weekend at room temperature. It was poured into water/NaCl and extracted with ether. The ether phase was dried with anhydrous magnesium sulfate, filtered, and concentrated in vacuo to 4.08 g orange oil. Proton NMR indicated this was a mixture. This product was purified by radial accelerated thin layer chromatography, first using 2% ethyl acetate/cyclohexane, and then 30% methylene chloride/cyclohexane. The best fractions were also recrystallized from hexanes to give 1.0 g of Compound 16 as a White solid (21% yield). m.p. 61°-64° C.

EXAMPLE 17

3-Pyridinecarboxylic acid, 2-(difluoromethyl)-5-(5-methyl-3-isothiazolyl)-4-(2-methylpropyl)-6-(trifluoromethyl)-, methyl ester.

The compound of Example 16 (2.0 g, 0.0051 mol), 60 mL methanol and one spatula portion of Raney Nickel catalyst (50% slurry in H$_2$O) were placed in a Parr bottle. This was put on the Parr Hydrogenator and pressurized to 46 psi (31.7 kiloPascals) H$_2$ (bottle pressure). After two hours, the bottle pressure had dropped to 40 psi (27.6 kiloPascals). The reaction mixture was filtered through celite to remove the Raney Nickel, and celite was washed with methanol. The filtrate was concentrated in vacuo to a yellow residue which was then dissolved in ether and washed with water/NaCl. The ether extract was dried with anhydrous magnesium sulfate, filtered, and concentrated in vacuo to a yellow solid (1.82 g). This was recrystallized from 10% ethyl acetate/hexanes to give 1.26 g of intermediate product, 3-pyridinecarboxylic acid, 5-(1-amino-3-oxo-1-butenyl)-2-(difluoromethyl)-4-(2-methylpropyl)-6-(trifluoromethyl)-, methyl ester, as an off-white solid (63% yield). m.p. 133°-135° C.

This intermediate compound (2.87 g, 0.0073 mol) was dissolved in 35 mL toluene. To this solution was added 3.37 g P$_4$S$_{10}$ (1 eq.) and 1.87 g chloranil (1 eq.). The reaction was refluxed for one hour at which time $^{19}$F-NMR showed complete reaction to one product. TLC (20% ethyl acetate/cyclohexane) showed multiple spots. The 35 reaction was washed with aqueous NaCl/NaHCO$_3$ and extracted with ether. The ether phase was dried with anhydrous magnesium sulfate, filtered, and concentrated n vacuo to a yellow liquid/solid. This was subjected to flash chromatography using 50% methylene chloride/cyclohexane as solvent. A yellow oil was recovered after concentrating the fractions in vacuo; it was contaminated with an unknown white solid. This product was dissolved in hexanes, and the solution decanted from the insoluble unknown solid. The hexanes solution was concentrated in vacuo to 2.6 g yellow oil.

EXAMPLE 18

3-Pyridinecarboxylic acid, 2-(difluoromethyl)-5-[4,5-dihydro-4-(methoxycarbonyl)-5-methyl-3-isoxazolyl]-4-(2-methylpropyl)-6-(trifluoromethyl)-, methyl ester.

The oxime compound of Example C (2.73 g, 0.0077 mol), 25 mL DMF and 1.34 g NCS (1.3 eq.) were heated together to 80° C. over a 10 minute period. Then heating was stopped, and the reaction gradually cooled to 30° C. over the next two hours. The reaction was poured in water and extracted with ether. The ether layer was washed several times with water (1000 mL total), dried with anhydrous magnesium sulfate, filtered, and concentrated in vacuo to 3.0 g chlorooxime (contains some residual ether). This was dissolved in 100 mL THF, and 1.2 mL triethylamine (1.1 eq.) was added. A white solid formed. The reaction was filtered through celite, and the pad was washed with THF. The filtrate was concentrated in vacuo to 2.5 g of the compound of Example D. This was dissolved in 40 mL toluene, followed by 1 mL methyl crotonate (0.0093 mol). The reaction was refluxed for 16 hours. Then it sat for several days at room temperature. TLC (20% ethyl acetate/cyclohexane) showed two product spots which were believed to be isomers. The toluene was removed in vacuo to give 3.2 g yellow oil. This was purified by radial accelerated thin layer chromatography (5% ethyl acetate/cyclohexane) to give 2.25 g product #1 (impure), 0.3 g product #2 (pure, solidified), and 0.5 g mixture of both products. The impure product #1 was further purified by radial accelerated thin layer chromatography (25% methylene chloride/cyclohexane increasing to 100% methylene chloride) to give 1.47 g of Compound 18 as a white solid (42% yield). m.p. 79°-83° C.

EXAMPLE 19

3-Pyridinecarboxylic acid, 2-(difluoromethyl)-5-[4,5-dihydro-5-(methoxycarbonyl)-4-methyl-3-isoxazolyl]-4-(2-methylpropyl)-6-(trifluoromethyl)-, methyl ester.

The product mixture from the initial radial accelerated thin layer chromatography run of Example 18 was further purified to collect more of product #2. It was combined with the 0.3 g already isolated for a total of 0.38 g of Compound 19, recovered as a white solid (11% yield) m.p. 114°-117° C.

EXAMPLE 20

3-Pyridinecarboxylic acid, 6-(difluoromethyl)-5-[4-(methoxycarbonyl)-3-isoxazolyl]-4-(2-methylpropyl)-2-(trifluoromethyl)-, methyl ester.

The oxime compound of Example A (3.5 g, 0.01 mol), 20 mL DMF, and 1.61 g NCS (1.2 eq.) were combined and heated to 80° C. during a 10-minute period. Then heating was stopped. The reaction gradually cooled to 30° C. over the next 1.5 hour. Then it was poured into water and extracted with ether. The ether phase was washed several times with more water (1000 mL total), then dried with anhydrous magnesium sulfate, filtered, and concentrated in vacuo to 3.8 g chlorooxime (contains residual ether). This was dissolved in 80 mL THF, followed by 1.7 g pyrrolidine enamine of methyl propiolate (1.1 eq.). The reaction was refluxed for 19 hours. There was some solid in the flask which was assumed to be pyrrolidine hydrochloride. The reaction was washed with water/NaCl and extracted with ether. The ether phase was dried with anhydrous magnesium sulfate, filtered, and concentrated in vacuo to 4.2 g orange oil. This was subjected to flash silica gel chromatography using 50% methylene chloride/cyclohexane as solvent. The appropriate fractions were concentrated n vacuo to give 3.3 g of Compound 20 as a white solid (75% yield). m.p. 82°-84° C.

EXAMPLE 21

3-pyridinecarboxylic acid, 5-(5-cyano-3-isoxazolyl)-2-(difluoromethyl)-4-(2-methylpropyl)-6-(trifluoromethyl)-, methyl ester.

A solution of 4 g (0.011 mol) of the compound in Example D, 2.7 mL (0.033 mol) 2-chloroacrylonitrile and 3 mL triethylamine in 100 mL THF was brought to reflux for 2 hours. The reaction was stirred at room temperature for 2 days and then was diluted with diethyl ether and washed successively with 3N HCl, a saturated sodium bicarbonate solution and finally with brine. The organics were dried over anhydrous magnesium sulfate and filtered through a silica pad. The resulting oil was purified on a Flash column in a 6/1 hexanes/ethyl acetate solvent system to yield Compound 21. m.p. 69°-70° C. Anal. Calcd. for $C_{17}H_{14}N_3O_3F_5$; C,50.63: H,3.50; N,10.42. Found: C,50.53; H,3.51; N,10.36.

EXAMPLE 22

3-Pyridinecarboxylic acid, 2-(difluoromethyl)-5-[4-(ethoxycarbonyl)-5-(trifluoromethyl)-3-isoxazolyl]-4-(2-methylpropyl)-6-(trifluoromethyl)-, methyl ester.

A solution of 4 g (0.011 mol) of the compound of Example D and 5.4 g (0.026 mol) 2-butenoic acid, 4,4,4-trifluoro-3-methoxy, ethyl ester, in dry toluene was refluxed overnight. The reaction mixture was diluted with diethyl ether and washed with a brine solution two times. The organic layer was dried over anhydrous magnesium sulfate and the volatiles were removed. The resultant dark yellow oil was purified by flash chromatography to give Compound 23 as an oil. Anal.Calcd. for $C_{20}H_{18}N_2O_5F_8$: C, 46.34; H, 3.30; N,5.40. Found: C, 46.62; H,3.51; N,5.33.

EXAMPLE 23

3-Pyridinecarboxylic acid, 2-(difluoromethyl)-5-[5-ethoxy-4-(ethoxycarbonyl)-3-isoxazolyl]-4-(2-methylpropyl)-6-(trifluoromethyl)-, methyl ester.

A solution of 4 g (0.011 mol) of the Compound of Example D and 2.1 mL (0.011 mol) ethyl 3,3-diethoxyacrylate in 80 mL THF was stirred for 12 hours at room temperature and then brought to reflux for one hour. The reaction mixture was diluted with diethyl ester and washed with 3N HCl, a saturated solution of sodium bicarbonate and finally with brine. The organics were dried over anhydrous magnesium sulfate and the volatiles were removed under vacuum. The compound was purified by Preparative LC using a 6:1 cyclohexanes/ethyl acetate solvent system. Anal. Calcd. for $C_{21}H_{23}N_2O_6F_5$: C,51.02; H,4.69; N,5.67. Found: C,50.90; H,4.60; N,5.75.

EXAMPLE 24

3-Pyridinecarboxylic acid, 5-(4,5-dichloro-4,5-dihydro-3-isoxazolyl)-2-(difluoromethyl)-4-(2-methylpropyl)-6-(trifluoromethyl)-, methyl ester, trans-.

Into 30 mL trans-1,2-dichloroethylene was added 3 g (0.0085 mol) of the compound of Example D. The reaction was stirred at room temperature for 4 hours, then 50 mL THF was added, and the reaction was stirred at reflux overnight. All volatiles were removed under vacuum and the residue was diluted with diethyl ether. The ether solution was washed three times with brine and then dried over anhydrous magnesium sulfate. The volatiles were removed under vacuum to give a solid which was recrystallized from ethanol and water, followed by further purification by Preparative LC to give a white solid with m.p. 89°-92° C. Anal. Calcd. for $C_{16}H_{15}N_2O_3F_5Cl_2$: C, 42.78; H,3.37; N, 6.24. Found: C, 43.20; H, 3.24; N, 6.17.

EXAMPLE 25

3-Pyridinecarboxylic acid, 5-(5-chloro-3-isoxazolyl)-2-(difluoromethyl)-4-(2-methylpropyl)-6-(trifluoromethyl)-, methyl ester.

Into 30 mL vinylidene chloride was added 3 g (0.0085 mol) of the compound of Example D. The reaction was brought to reflux for 4 hours and then 50 mL THF was added and the reaction refluxed for an additional 12 hours. The reaction mixture was diluted with diethyl ether and washed three times with brine. The organics were dried over anhydrous magnesium sulfate and the volatiles removed under vacuum. The remaining material contained a mixture of the isoxazole and the un-eliminated isoxazoline. The material was diluted in methanol and stirred in the presence of sodium methoxide for 4 hours. The reaction was again diluted with diethyl ether and washed with brine. The organic layers were dried over anhydrous magnesium sulfate and the volatiles removed to give an oil which was purified by flash chromatography to give Compound 25 as a solid. m.p. 37° C. Anal. Calcd. for $C_{17}H_{14}N_3O_3F_5$: C,50.63; H,3.50; N,10.42. Found: C,50.53; H,3.51; N,10.36.

EXAMPLE 26

3-Pyridinecarboxylic acid, 5-(4-cyano-3-isoxazolyl)-2-(difluoromethyl)-4-(2-methylpropyl)-6-(trifluoromethyl)-, methyl ester.

A solution of 3 g (0.0085 mol) of the compound of Example D and 0.876 mL (0.0085 mol) ethoxy acrylonitrile in 100 mL THF was refluxed 20 hours. The reaction was diluted with diethyl ether and washed three times with brine. The organics were dried over anhydrous magnesium sulfate and the volatiles were removed. The resultant oil was purified on preparative LC to give 0.6 g (.00148 mol) of Compound 26. m.p. 76°-78° C. Anal. Calcd. for $C_{17}H_{20}N_3O_4F_5$: C,50.63; H,3.50; N,10.42. Found: C,50.56; H,3.48; N,10.40.

EXAMPLE 27

3-Pyridinecarboxylic acid, 5-(4-chloro-3-isoxazolyl)-2-(difluoromethyl)-4-(2-methylpropyl)-6-(trifluoromethyl)-, methyl ester.

A solution of 0.8 g (0.0017 mol) of Compound 24 and 200 mg solid sodium methylate in 10 mL methanol was stirred overnight at room temperature. The solution was diluted with diethyl ether and washed two times with brine. The organics were dried over anhydrous magnesium sulfate and the volatiles were removed under vacuum to give a yellow oil which was loaded onto a flash column using a 9:1 cyclohexanes/ethyl acetate solvent system for purification. Anal. Calcd. for $C_{16}H_{14}N_2O_3F_5Cl_1$: C,46.56; H,3.42; N,6.79. Found: C,46.42; H,3.42; N,6.72.

EXAMPLE 28

3-Pyridinecarboxylic acid, 5-(5-cyano-3-isoxazolyl)-4-(cyclopropylmethyl)-2-(difluoromethyl)-6-(trifluoromethyl)-, methyl ester.

A solution of 3.5 g (0.0099 mol) of 3-pyridinecarboxylic acid, 5-cyano-4-(cyclopropylmethyl)-2-(difluoromethyl)-6-(trifluoromethyl)-, methyl ester, N-oxide, prepared from the corresponding aldehyde according to the procedure of Examples C and D, and 2.6 g (0.029 mol) 2-chloroacrylonitrile in 80 mL THF was brought to reflux for 3 hours. The reaction was diluted with diethyl ether and washed three times with brine. The organics were dried over anhydrous magnesium sulfate and the volatiles removed to give 3 g of crude product which was purified by Preparative LC using a 9:1 cyclohexanes/ethyl acetate solvent system. Anal. Calcd. for $C_{17}H_{12}N_3O_3F_5$: C,50.88; H,3.01; N,10.47. Found: C,50.53; H,3.13; N,9.94.

EXAMPLE 29

4,5-Isoxazoledicarboxylic acid, 3-[4-(cyclopropylmethyl)-6-(difluoromethyl)-5-(methoxycarbonyl)-2-(trifluoromethyl)-3-pyridinyl]-, dimethyl ester.

A solution of 12 g (0.034 mol) of the nitrile oxide used in Example 28 and 4.86 g (0.034 mol) dimethyl acetylenedicarboxylate in 150 mL THF was refluxed for four hours. The solution was diluted with diethyl ether and washed three times with brine. The organics were dried over anhydrous magnesium sulfate and the volatiles were removed under vacuum. The resultant oil was diluted into a 3 cyclohexanes to 1 ethyl acetate solvent mixture and filter through a 3 inch silica pad to yield Compound 29 as a solid. m.p. 53°–54° C. Anal. Calcd. for $C_{20}H_{17}N_2O_7F_5$: C,48.79; H,3.48; N,5.69. Found: C,48.89, N,5.64.

EXAMPLE 30

3-Pyridinecarboxylic acid, 5-(4,5-dichloro-4,5-dihydro-3-isoxazolyl)-2-(difluoromethyl)-4-(2-methylpropyl)-6-(trifluoromethyl)-, ethyl ester, trans-.

Compound 30 was made in the same manner as in Example 24 using 6 g (0.016 mol) of 3-pyridinecarboxylic acid, 5-cyano-2-(difluoromethyl)-4-(2-methylpropyl)-6-(trifluoromethyl)-, ethyl ester, N-oxide, prepared from the corresponding aldehyde, following the procedure of Examples C and D, and 30 mL transdichloroethylene. The compound was purified by Preparative LC using a 9:1 hexanes/ethyl acetate solvent system to yield Compound 30 as a solid. m.p. 65°–66° C. Anal. Calcd. for $C_{17}H_{17}N_2O_3F_5Cl_2$: C,44.08; H,3.70; N,6.05. Found: C,44.23; H,3.74; N,6.07.

EXAMPLE 31

3-Pyridinecarboxylic acid, 2-(difluoromethyl)-5-(3-isoxazolyl)-4-(2-methylpropyl)-6-(trifluoromethyl).

A solution of 5 g (0.013 mol) of the Compound of Example 9 in ethanol and 1 g (0.026 mol) sodium hydroxide dissolved in 5 mL water was stirred at room temperature overnight. The reaction mixture was poured onto a 1N HCl/ice solution and then extracted into diethyl ether. The organics were dried over anhydrous magnesium sulfate and the volatiles removed to give Compound 31 as a yellow solid. m.p. 72°–73° C. Anal. Calcd. for $C_{15}H_{13}N_2O_3F_5$: C,49.46; H,3.60; N,7.69. Found: C,49.24; H,3.65; N,7.63.

EXAMPLE 32

3-Pyridinecarboxylic acid, 2-(difluoromethyl)-5-(4-methyl-3-isoxazolyl)-4-(2-methylpropyl)-6-(trifluoromethyl)-, methyl ester.

Into a round bottom flask were added 110 g (0.312 mol) of the compound of Example D and 400 mL of a cis/trans mixture of 1-ethoxypropene. An initial exotherm was observed and the reaction had to be cooled in an ice bath. The reaction was stirred overnight to give two products in the ratio of 7:3. A semi-solid remained after all volatiles were pulled off that was taken directly on to the next step. The crude reaction products were added directly to a freshly prepared solution of 7.1 g (0.308 mol) of sodium dissolved in a 1.5 L methanol. The reaction was stirred for 20 hours at which time all of the major isomer of the starting material had been converted over to a new product. The minor isomer remained unchanged. The mixture was diluted in diethyl ether after most of the methanol had been removed under vacuum, and the ether layer was washed two times with brine. The organics were dried over anhydrous magnesium sulfate and the volatiles removed to give 130 g of a milky yellow oil. The product was purified away from the minor isomer by successive recrystallizations from hot ethanol. The impurity recrystallizes away from the product, and the remaining mother liquor contained 80 g of Compound 32. Anal. Calcd. for $C_{15}H_{12}N_2O_2F_5Cl_1$: C, 47.08; H,3.16; N,7.32. Found: C,47.29; H,3.21); N, 7.25.

EXAMPLE 33

3-Pyridinecarboxylic acid, 2-(difluoromethyl)-5-(4-ethoxy-4,5-dihydro-5-methyl-3-isoxazolyl)-4-(2-methylpropyl)-6-(trifluoromethyl), methyl ester, trans.

The impurity of Example 32 was isolated as a solid. m.p. 114° C. Anal. Calcd. for $C_{19}H_{24}N_2O_4F_5$: C,52.06; H,5.29; N,6.39. Found: C,52.16; H,5.30; N,6.40.

EXAMPLE 34

3-Pyridinecarboxylic acid, 5-[4,5-dihydro-5-(phenylsulfonyl)-3-isoxazolyl]-2-methoxy-4-(2-methylpropyl)-6-(trifluoromethyl)-, methyl ester.

A solution of 3-pyridinecarboxylic acid, 5-[(hydroxyimino)methyl]-2-methoxy-4-(2-methylpropyl)-6-trifluoromethyl)-, methyl ester, prepared from the corresponding aldehyde following the procedures of Examples C and D, (10 g, 0.029 mol) and 4.8 g (0.035 mol) NCS in 100 mL DMF was stirred at 70° C. for 1.5 hours. The reaction was diluted with diethyl ether and washed three times with brine. The organics were dried over anhydrous magnesium sulfate and the volatiles removed to give 10.9 g of the crude chlorooxime. The chlorooxime was diluted in 100 mL THF and 5.1 g (0.30 mol phenyl vinyl sulfone was added, followed by 3 g (0.030 mol) triethylamine. A white solid precipitated and the mixture was refluxed overnight. The reaction mixture was diluted with diethyl ether and washed with brine. The organics were dried over anhydrous magnesium sulfate and the volatiles were removed under vacuum to give a brown oil which was purified by Preparative LC using a 5:1 cyclohexanes/ethyl acetate solvent system to yield Compound 34 as a solid. m.p. 105°–106° C.

EXAMPLE 35

3-Pyridinecarboxylic acid, 5-(3-isoxazolyl)-2-methoxy-4-(2-methylpropyl)-6-(trifluoromethyl)-, methyl ester.

A solution of 0.8 g (0.0015 mol) of Compound 34 and 0.5 g solid sodium methylate in methanol was stirred for two days. The solution was diluted in diethyl ether and washed two times with brine. The organics were dried over anhydrous magnesium sulfate and the volatiles were removed under vacuum to give an oil which was purified by preparative LC in a 9:1 cyclohexanes/ethyl acetate solvent system to yield Compound 35 as a solid. m.p. 71°–72° C.

EXAMPLE 36

3-Pyridinecarbonyl chloride, 2-(difluoromethyl)-5-(3-isoxazolyl)-4-(2-methylpropyl)-6-(trifluoromethyl)-.

A slurry of 2.8 g (0.0076 mol) of Compound 31 and 1.6 g (0.0076 mol) phosphorous pentachloride in 50 mL carbon tetrachloride was stirred at room temperature for 4 hours and then at reflux for one hour. The volatiles were evaporated under vacuum to yield 3 g of an orange solid. The solid was dissolved in a mixture of 3 parts hexanes to 1 part ethyl acetate and filtered through silica to yield Compound 35 as a solid. m.p. 83°–85° C.

EXAMPLE 37

3-Pyridinecarbothioic acid, 2-(difluoromethyl)-5-(3-isoxazolyl)-4-(2-methylpropyl)-6-(trifluoromethyl)-, S-methyl ester.

Compound 36 (1 g, 0.0026 mol) was dissolved in 50 mL THF and 0.27 g (0.0039 mol) sodium methanethiolate was added. The solution was stirred overnight at room temperature and then diluted with diethyl ether and washed two times with 2.5N sodium hydroxide solution. The organics were dried over anhydrous magnesium sulfate and the volatiles removed under vacuum. The product was purified by preparative LC in a 3:1 hexanes/ethyl acetate solvent system to yield Compound 37. Anal. Calcd. for $C_{16}H_{15}N_2O_2F_5S_1$: C,48.73; H,3.83; N,7.10. Found: C,48.84; H,3.86; N,7.07.

The following is a listing by Example number and nomenclature of compounds herein.

| Compound No. | Name |
| --- | --- |
| 1 | 4,5-Isoxazoledicarboxylic acid, 3-[6-(difluoromethyl)-5-(methoxycarbonyl)-4-(2-methylpropyl)-2-(trifluoromethyl)-3-pyridinyl]-, dimethyl ester |
| 2 | 4,5-Isoxazoledicarboxylic acid, 3-[2-(difluoromethyl)-5-(methoxycarbonyl)-4-(2-methylpropyl)-6-(trifluoromethyl)-3-pyridinyl]-4,5-dihydro-, dimethyl ester |
| 3 | 4,5-Isoxazoledicarboxylic acid, 3-[6-(difluoromethyl)-5-(methoxycarbonyl)-4-(2-methylpropyl)-2-(trifluoromethyl)-3-pyridinyl]-4,5-dihydro-, dimethyl ester |
| 4 | 3-Pyridinecarboxylic acid, 2-(difluoromethyl)-5-[4-(ethoxycarbonyl)-3-isoxazolyl]-4-(2-methylpropyl)-6-(trifluoromethyl)-, methyl ester |
| 5 | 3-Pyridinecarboxylic acid, 2-(difluoromethyl)-5-[4,5-dihydro-5-(methoxycarbonyl)-3-isoxazolyl]-4-(2-methylpropyl)-6-(trifluoromethyl)-, methyl ester |
| 6 | 3-Pyridinecarboxylic acid, 6-(difluoromethyl)-5-(3-isoxazolyl)-4-(2-methylpropyl)-2-(trifluoromethyl)-, methyl ester |
| 7 | 3-Pyridinecarboxylic acid, 2-(difluoromethyl)-5-(4,5-dihydro-3-isoxazolyl)-4-(2-methylpropyl)-6-(trifluoromethyl)-, methyl ester |
| 8 | 3-Pyridinecarboxylic acid, 2-(difluoromethyl)-5-[5-(methoxycarbonyl)-3-isoxazolyl]-4-(2-methylpropyl)-6-(trifluoromethyl)-, methyl ester |
| 9 | 3-Pyridinecarboxylic acid, 2-(difluoromethyl)-5-(3-isoxazolyl)-4-(2-methylpropyl)-6-(trifluoromethyl)-, methyl ester |
| 10 | 3-Pyridinecarboxylic acid, 2-(difluoromethyl)-5-[4-(methoxycarbonyl)-3-isoxazolyl]-4-(2-methylpropyl)-6-(trifluoromethyl)-, methyl ester |
| 11 | 3-Pyridinecarboxylic acid, 2-(difluoromethyl)-5-[5-(ethoxycarbonyl)-3-isoxazolyl]-4-(2-methylpropyl)-6-(trifluoromethyl)-, methyl ester |
| 12 | 3-Pyridinecarboxylic acid, 2-(difluoromethyl)-5-[5-(ethoxycarbonyl)-4,5-dihydro-3-isoxazolyl]-4-(2-methylpropyl)-6-(trifluoromethyl)-, methyl ester |
| 13 | 3-Pyridinecarboxylic acid, 2-(difluoromethyl)-5-(4,5-dihydro-5-methoxy-3-isoxazolyl)-4-(2-methylpropyl)-6-(trifluoromethyl)-, methyl ester |
| 14 | 3-Pyridinecarboxylic acid, 2-(difluoromethyl)-5-(4,5-dihydro-5-methyl-3-isoxazolyl)-4-(2-methylpropyl)-6-(trifluoromethyl)-, methyl ester |
| 15 | 3-Pyridinecarboxylic acid, 2-(difluoromethyl)-5-(5-ethoxy-4,5-dihydro-3-isoxazolyl)-4-(2-methylpropyl)-6-(trifluoromethyl)-, methyl ester |
| 16 | 3-Pyridinecarboxylic acid, 2-(difluoromethyl)-5-(5-methyl-3-isoxazolyl)-4-(2-methylpropyl)-6-(trifluoromethyl)-, methyl ester |
| 17 | 3-Pyridinecarboxylic acid, 2-(difluoromethyl)-5-(5-methyl-3-isothiazolyl)-4-(2-methylpropyl)-6-(trifluoromethyl)-, methyl ester |
| 18 | 3-Pyridinecarboxylic acid, 2-(difluoromethyl)-5-[4,5-dihydro-4-(methoxycarbonyl)-5-methyl-3-isoxazolyl]-4-(2-methylpropyl)-6-(trifluoromethyl)-, methyl ester |
| 19 | 3-Pyridinecarboxylic acid, 2-(difluoromethyl)-5-[4,5-dihydro-5-(methoxycarbonyl)-4-methyl-3-isoxazolyl]-4-(2-methylpropyl)-6-(trifluoromethyl)-, methyl ester |
| 20 | 3-Pyridinecarboxylic acid, 6-(difluoromethyl)-5-[4-(methoxycarbonyl)-3-isoxazolyl]-4-(2-methylpropyl)-6-(trifluoromethyl)-, methyl ester |
| 21 | 3-Pyridinecarboxylic acid, 5-(5-cyano-3-isoxazolyl)-2-(difluoromethyl)-4-(2-methylpropyl)-6-(trifluoromethyl)-, methyl ester |
| 22 | 3-Pyridinecarboxylic acid, 2-(difluoromethyl)-5-[4-(ethoxycarbonyl)-5-(trifluoromethyl)-3-isoxazolyl]-4-(2-methylpropyl)-6-(trifluoromethyl)-, methyl |

-continued

| Compound No. | Name |
|---|---|
| 23 | 3-Pyridinecarboxylic acid, 2-(difluoromethyl)-5-[5-ethoxy-4-(ethoxycarbonyl)-3-isoxazolyl]-4-(2-methylpropyl)-6-(trifluoromethyl)-, methyl ester |
| 24 | 3-Pyridinecarboxylic acid, 5-(4,5-dichloro-4,5-dihydro-3-isoxazolyl)-2-(difluoromethyl)-4-(2-methylpropyl)-6-(trifluoromethyl)-, methyl ester, trans- |
| 25 | 3-Pyridinecarboxylic acid, 5-(5-chloro-3-isoxazolyl)-2-(difluoromethyl)-4-(2-methylpropyl)-6-(trifluoromethyl)-, methyl ester |
| 26 | 3-Pyridinecarboxylic acid, 5-(4-cyano-3-isoxazolyl)-2-(difluoromethyl)-4-(2-methylpropyl)-6-(trifluoromethyl)-, methyl ester |
| 27 | 3-Pyridinecarboxylic acid, 5-(4-chloro-3-isoxazolyl)-2-(difluoromethyl)-4-(2-methylpropyl)-6-(trifluoromethyl)-, methyl ester |
| 28 | 3-Pyridinecarboxylic acid, 5-(5-cyano-3-isoxazolyl)-4-(cyclopropylmethyl)-2-(difluoromethyl)-6-(trifluoromethyl)-, methyl ester |
| 29 | 4,5-Isoxazoledicarboxylic acid, 3-[4-(cyclopropylmethyl)-6-(difluoromethyl)-5-(methoxycarbonyl)-2-(trifluoromethyl)-3-pyridinyl]-, dimethyl ester |
| 30 | 3-Pyridinecarboxylic acid, 5-(4,5-dichloro-4,5-dihydro-3-isoxazolyl)-2-(difluoromethyl)-4-(2-methylpropyl)-6-(trifluoromethyl)-, ethyl ester, trans- |
| 31 | 3-Pyridinecarboxylic acid, 2-(difluoromethyl)-5-(3-isoxazolyl)-4-(2-methylpropyl)-6-(trifluoromethyl)- |
| 32 | 3-Pyridinecarboxylic acid, 2-(difluoromethyl)-5-(4-methyl-3-isoxazolyl)-4-(2-methylpropyl)-6-(trifluoromethyl)-, methyl ester |
| 33 | 3-Pyridinecarboxylic acid, 2-(difluoromethyl)-5-(4-ethoxy-4,5-dihydro-5-methyl-3-isoxazolyl)-4-(2-methylpropyl)-6-(trifluoromethyl)-, methyl ester, trans- |
| 34 | 3-Pyridinecarboxylic acid, 5-[4,5-dihydro-5-(phenylsulfonyl)-3-isoxazolyl]-2-methoxy-4-(2-methylpropyl)-6-(trifluoromethyl)-, methyl ester |
| 35 | 3-Pyridinecarboxylic acid, 5-(3-isoxazolyl)-2-(methoxy)-4-(2-methylpropyl)-6-(trifluoromethyl)-, methyl ester |
| 36 | 3-Pyridinecarbonyl chloride, 2-(difluoromethyl)-5-(3-isoxazolyl)-4-(2-methylpropyl)-6-(trifluoromethyl)- |
| 37 | 3-Pyridinecarbothioic acid, 2-(difluoromethyl)-5-(3-isoxazolyl)-4-(2-methylpropyl)-6-(trifluoromethyl)-, S-methyl ester |

PRE-EMERGENT ACTIVITY ON PLANTS

As noted above, compounds of this invention have been found to be effective as herbicides, particularly pre-emergent herbicides. Tables A and B summarize results of tests conducted to determine the pre-emergent herbicidal activity of the compounds of this invention. The herbicidal activity data in Tables A and B are based on the percent inhibition of each tested plant species. The term "C" designates complete control of the plant species.

One set of pre-emergent tests was conducted as follows:

Topsoil was placed in a pan and compacted to a depth of 0.95 to 1.27 cm. from the top of the pan. A predetermined number of seeds of each of several monocotyledonous and dicotyledonous annual plant species and/or vegetative propagules of various perennial plant species were placed on top of the soil. The soil required to level fill a pan after seeding or adding vegetative propagules was weighed into another pan. A known amount of the test compound dissolved or suspended in an organic solvent or water and applied in acetone or water as a carrier was thoroughly mixed with this cover soil, and the herbicide/soil mixture was used as a cover layer for the previously prepared pan. In Table A below the amounts of active ingredient were all equivalent to an application rate of 11.2 kilograms/hectare (kg/ha). After treatment, the pans were moved to a greenhouse bench where they were watered as needed to give adequate moisture for germination and growth.

Approximately 10–14 days (usually 11 days) after planting and treating, the plants were observed and the results recorded.

The treated plant species are identified by letter headings printed vertically above the columns according to the following legend:

ANBG - Annual Bluegrass
BARZ - Barley
BLGR - Blackgrass
BYGR - Barnyardgrass
CIWE - Jimsonweed
COBU - Cocklebur
COCW - Common Chickweed
CORN - Corn
COTZ - Cotton
CWBS - Catchweed Bedstraw
DOBR - Downy Brome
GRFT - Green Foxtail
GRSO - Grain Sorghum
HESE - Hemp Sesbania
INMU - Indian Mustard
LACG - Large Crabgrass
MOGL - Morningglory
PRMI - Proso Millet
RAPE - Oilseed Rape
RICE - Rice
RUTH - Russian Thistle
SEJG - Seedling Johnsongrass
SOBE - Soybean
VELE - Velvetleaf
WHEZ - Wheat
WIBW - Wild Buckwheat
WIOA - Wild Oats
YENS - Yellow Nutsedge

TABLE A

| | | Herbicide Primary Preemergence | | | | | | | | | |
|---|---|---|---|---|---|---|---|---|---|---|---|
| CP No. | Rate kg/ha | Yens | Anbg | Sejg | Dobr | Bygr | Mogl | Cobu | Vele | Inmu | Wibw |
| 1 | 11.21 | 0 | 90 | 40 | 0 | 90 | 30 | 0 | 0 | 0 | 0 |
| | 11.21 | 0 | 90 | 50 | 10 | 90 | 10 | 0 | 20 | 0 | 0 |
| 2 | 11.21 | 0 | 90 | 90 | 0 | 90 | 0 | 0 | 0 | 0 | 0 |
| 3 | 11.21 | 50 | C | C | C | C | 80 | 70 | 90 | C | C |
| | 11.21 | 60 | C | C | C | 90 | 80 | 20 | 80 | C | 90 |
| 4 | 11.21 | 80 | C | C | 90 | C | 90 | 10 | 80 | 90 | 90 |
| | 11.21 | 90 | C | C | C | C | 90 | 50 | 90 | C | C |
| 5 | 11.21 | 0 | 90 | 60 | 0 | 90 | 0 | 0 | 0 | 30 | 20 |
| | 11.21 | 0 | C | 90 | 0 | 90 | 0 | 0 | 50 | 30 | 60 |
| 6 | 11.21 | 70 | C | C | 90 | C | 80 | 0 | 80 | C | 90 |
| 7 | 11.21 | 80 | C | C | 90 | C | 90 | 50 | C | C | C |
| 8 | 11.21 | 0 | 60 | 30 | 0 | 70 | 10 | 40 | 0 | 0 | 0 |
| 9 | 11.21 | 90 | C | C | C | C | C | 60 | 90 | C | C |
| 10 | 11.21 | C | C | C | C | C | C | 90 | 90 | C | C |
| 11 | 11.21 | 0 | C | 80 | 0 | 90 | 0 | 70 | 0 | 0 | 0 |

TABLE A-continued

| | | Herbicide Primary Preemergence | | | | | | | | |
|---|---|---|---|---|---|---|---|---|---|---|
| CP No. | Rate kg/ha | Yens | Anbjg | Sejg | Dobr | Byggr | Mogl | Colu | Vele | Inmu | Wibw |
| 12 | 11.21 | 0 | C | 90 | 0 | 90 | 20 | 0 | 0 | 0 | 0 |
| 13 | 11.21 | 80 | C | C | 90 | C | 90 | 0 | 80 | 90 | 90 |
| 14 | 11.21 | C | C | C | 90 | C | 90 | 0 | 90 | C | 90 |
| 15 | 11.21 | 70 | C | C | 90 | C | 80 | 0 | 90 | 90 | 90 |
| 16 | 11.21 | C | C | C | C | C | C | 70 | 90 | C | C |
| 17 | 11.21 | 0 | C | C | 90 | C | 90 | 70 | 90 | C | C |
| 18 | 11.21 | C | C | C | C | C | 90 | 80 | C | C | C |
| 19 | 11.21 | 0 | C | 10 | 80 | 90 | 0 | 0 | 60 | 30 | 30 |
| 20 | 11.21 | 0 | C | C | 90 | C | 80 | 0 | 90 | C | 90 |
| 21 | 11.21 | 0 | C | 90 | 70 | C | 60 | 20 | 70 | 70 | 60 |
| 22 | 11.21 | 10 | C | C | C | C | 30 | 10 | 60 | 90 | 80 |
| 23 | 11.21 | 0 | C | 60 | 40 | 90 | 10 | 0 | 0 | 40 | 10 |
| 24 | 11.21 | 40 | C | C | C | C | 80 | 70 | 90 | C | C |
| 25 | 11.21 | 0 | C | C | C | C | 90 | 60 | 90 | C | 90 |
| 26 | 11.21 | C | C | C | C | C | 90 | 60 | 90 | C | C |
| 27 | 11.21 | 90 | C | C | C | C | C | 40 | 90 | C | 90 |
| 28 | 11.21 | 0 | C | 90 | 0 | C | 90 | 0 | 60 | 60 | 80 |
| 29 | 11.21 | 20 | C | C | C | C | 80 | 10 | 80 | C | C |
| 30 | 11.21 | 0 | C | C | 90 | C | 70 | 10 | 70 | C | C |
| 31 | 11.21 | 0 | 90 | 80 | 0 | 90 | 10 | 0 | 0 | 40 | 0 |
| 32 | 11.21 | C | C | C | C | C | C | 40 | 90 | C | C |
| 33 | 11.21 | 0 | C | C | 90 | C | 50 | 20 | 20 | C | C |
| 34 | 11.21 | 0 | 30 | 50 | 10 | 70 | 0 | 0 | 0 | 0 | 0 |
| 35 | 11.21 | 90 | C | C | C | C | 90 | 20 | C | C | C |
| 36 | 11.21 | 0 | 0 | 0 | 0 | 0 | 0 | 0 | 0 | 0 | 0 |
| 37 | 11.21 | 80 | C | C | 90 | C | 80 | 20 | 80 | C | C |

In another set of tests, the pre-emergence activity of compounds of this invention was tested on weeds in the presence of crop plants. In these tests the following procedure was used:

Topsoil was sieved to pass through a 1.27 cm screen. Fertilizer was added to the topsoil in some of the tests, while in testing other compounds the fertilizer was omitted. The mixture was then sterilized by exposure to methyl bromide or by heating.

The topsoil mixture was placed in individual aluminum pans and compacted to a depth of about 1.27 cm from the top of the pan. A predetermined number of seeds of each of several monocotyledonous and dicotyledonous plant species and, where noted, vegetative propagules of various perennial plant species were slanted in the pans. The soil required to level fill a pan after seeding or adding vegetative propagules was weighed into another pan. A known amount of the test compound was dissolved or suspended in acetone or a suitable organic solvent as a 1% solution or suspension and applied to the cover soil using a sprayer at the desired rate. The spray was thoroughly mixed with this cover soil, and the herbicide/soil mixture was used as a cover layer for the previously prepared pan. Untreated soil was used as a cover layer for control pans. In Table B below the amount of active ingredient applied is shown. After treatment, the pans were moved to a greenhouse bench. Moisture was supplied to each pan as needed for germination and growth. Growth of each species was observed and corrective measures (greenhouse fumigation, insecticide treatment, and the like) were applied as needed. Approximately 10–14 days (usually 11 days) after planting and treating, the plants were observed and the results recorded.

The pre-emergence data for weeds in the presence of crop plants are shown in the following Table B.

TABLE B

| | | Herbicide Secondary Preemergence | | | | | | | | | | | | | | | | | | | | | | |
|---|---|---|---|---|---|---|---|---|---|---|---|---|---|---|---|---|---|---|---|---|---|---|---|---|
| CP No. | Rate kg/ha | Sobe | Cotz | Rape | Cwbu | Wibw | Mogl | Hese | Cviwe | Vele | Wrhc | Rize | Gcro | Cobn | Dobr | Prmi | Bygr | Lrfgt | Gccw | Abbg | Burzh | Reja | Swoba | Cwbs | Blgr |
| 1 | 5.6050 | 0 | 0 | 15 | 0 | 15 | 0 | 0 | 15 | 0 | 0 | 20 | 45 | 20 | 0 | 0 | C | 80 | 85 | — | — | — | — | — | — |
| | 1.1210 | 0 | 0 | 0 | 0 | 0 | 0 | 0 | 10 | 0 | 0 | 15 | 30 | 0 | 0 | 0 | 0 | 25 | 0 | — | — | — | — | — | — |
| | 0.2803 | 0 | 0 | 10 | 0 | 0 | 0 | 0 | 0 | 0 | 0 | 15 | 35 | 5 | 0 | 0 | 0 | 15 | 0 | — | — | — | — | — | — |
| 2 | 5.6050 | 25 | 0 | 0 | 0 | 45 | 0 | 0 | — | 0 | 30 | 30 | 0 | 20 | 30 | 75 | 70 | 95 | 15 | 50 | — | — | — | — | — |
| | 1.1210 | 0 | 25 | 0 | 0 | 65 | 0 | 0 | — | 0 | 0 | 0 | 0 | 0 | 0 | 0 | 0 | 55 | 0 | 40 | — | — | — | — | — |
| | 0.2803 | 0 | N | 0 | 0 | 0 | 0 | 0 | — | 0 | 0 | 0 | 0 | 0 | 0 | 0 | 0 | 0 | 0 | 0 | — | — | — | — | — |
| 3 | 5.6050 | 95 | 45 | 95 | 35 | 95 | 90 | 90 | — | 90 | C | 85 | C | 95 | C | C | C | C | C | C | — | — | — | — | — |
| | 1.1210 | 90 | 35 | 90 | 25 | C | 85 | 90 | — | 90 | 90 | 55 | C | 90 | C | C | C | C | C | C | — | — | — | — | — |
| | 0.2803 | 15 | 50 | 35 | 0 | 60 | 20 | 15 | — | 55 | 40 | 40 | 65 | 30 | 35 | 90 | 95 | 95 | 95 | C | — | — | — | — | — |
| | 0.0701 | 10 | 40 | 0 | 0 | 30 | 0 | 0 | — | 0 | 10 | 55 | 0 | 40 | 0 | 0 | 0 | 85 | 10 | 80 | — | — | — | — | — |
| | 0.0175 | 0 | 0 | 0 | 0 | 0 | 0 | 0 | — | 0 | 0 | 0 | 0 | 0 | 0 | 0 | 0 | 35 | 0 | 0 | — | — | — | — | — |
| | 0.0087 | N | 0 | 0 | 0 | 0 | 0 | N | — | N | 0 | 0 | 0 | 0 | 0 | 0 | 0 | 0 | 0 | 0 | — | — | — | — | — |
| 4 | 5.6050 | 90 | 65 | 95 | 0 | 95 | 90 | 90 | — | 90 | C | 80 | C | 90 | C | C | C | C | C | C | — | — | — | — | — |
| | 1.1210 | 75 | 35 | 90 | 25 | 95 | 90 | 85 | — | 90 | 90 | 85 | 99 | 90 | C | C | C | C | C | C | — | — | — | — | — |
| | 0.2803 | 20 | 30 | 30 | 0 | 75 | 75 | 40 | — | 50 | 55 | 55 | 90 | 45 | 90 | 85 | 95 | 95 | 95 | C | — | — | — | — | — |
| | 0.0701 | 0 | 0 | 0 | 0 | 25 | 0 | 0 | — | 0 | 45 | 15 | 25 | 20 | 35 | 0 | 35 | 90 | 35 | 90 | — | — | — | — | — |
| | 0.0175 | 25 | 0 | 0 | 0 | 20 | 0 | 0 | — | 0 | 20 | 0 | 0 | 25 | 0 | 0 | 0 | 75 | 0 | 45 | — | — | — | — | — |
| | 0.0087 | 0 | 0 | 0 | 0 | 0 | 0 | 0 | — | 0 | 0 | 10 | 0 | 20 | 0 | 0 | N | 65 | N | 35 | — | — | — | — | — |
| 5 | 5.6050 | 25 | 15 | 25 | 0 | 75 | 0 | 35 | — | 40 | 30 | 0 | 0 | 5 | 35 | 60 | 75 | 95 | 70 | 80 | — | — | — | — | — |
| | 1.1210 | 40 | 20 | 0 | 0 | 0 | 0 | 0 | — | 0 | 0 | 0 | 0 | 0 | 0 | 0 | 0 | 70 | 0 | 60 | — | — | — | — | — |
| | 0.2803 | 0 | 0 | 0 | 0 | 25 | 0 | 0 | — | 0 | 0 | 0 | 0 | 0 | 40 | 0 | 0 | 0 | 0 | 30 | — | — | — | — | — |
| 6 | 5.6050 | 85 | 0 | 80 | 30 | C | 95 | 85 | — | 85 | C | 95 | C | 95 | 95 | C | C | C | C | C | — | — | — | — | — |
| | 1.1210 | 85 | 0 | 50 | 40 | 95 | 95 | 75 | — | 80 | C | 60 | C | 80 | C | C | C | C | C | C | — | — | — | — | — |
| | 0.2803 | 30 | 0 | 15 | 0 | 45 | 50 | 30 | — | 35 | 55 | 50 | 90 | 60 | 50 | C | 98 | C | 90 | 55 | — | — | — | — | — |
| | 0.0175 | 0 | 0 | 0 | 0 | 0 | 0 | 0 | — | 10 | 0 | 0 | 25 | 20 | 0 | 0 | 20 | 0 | 15 | 30 | — | — | — | — | — |
| | 0.0087 | 15 | 0 | 0 | 0 | 0 | 0 | 0 | — | 0 | 0 | 0 | 0 | 0 | 0 | 0 | 0 | 0 | 0 | 0 | — | — | — | — | — |
| 7 | 5.6050 | 95 | 75 | C | 45 | C | 95 | 75 | — | C | C | C | C | C | C | C | C | C | C | C | — | — | — | — | — |
| | 1.1210 | 99 | 15 | 95 | 0 | 95 | C | 95 | — | C | C | C | C | C | C | C | C | C | C | C | — | — | — | — | — |
| | 0.2803 | 90 | 10 | 95 | 0 | C | 90 | 90 | — | 95 | 85 | 98 | 99 | 95 | C | C | C | C | 95 | C | — | — | — | — | — |
| | 0.0701 | 55 | 5 | 30 | 0 | 35 | 30 | 35 | — | 65 | 30 | 55 | 90 | 35 | 98 | C | 90 | C | 90 | 45 | — | — | — | — | — |
| | 0.0175 | 0 | 0 | 0 | N | 30 | 5 | 0 | — | 30 | 45 | 0 | 75 | 20 | 25 | 98 | 90 | 90 | 70 | 50 | — | — | — | — | — |
| | 0.0087 | 20 | 10 | 10 | 30 | 0 | 35 | 0 | — | 0 | 0 | 5 | 35 | 25 | 0 | 30 | 95 | 90 | 75 | 45 | — | — | — | — | — |
| 9 | 5.6050 | 95 | 80 | C | 80 | C | 98 | 95 | — | 95 | C | C | C | C | C | C | C | C | C | C | — | — | — | — | — |
| | 1.1210 | 95 | 25 | 95 | 0 | 95 | 90 | 95 | — | 95 | C | 95 | C | 90 | C | C | C | C | C | C | — | — | — | — | — |
| | 0.2803 | 85 | 20 | 90 | 0 | 95 | 90 | 90 | — | C | C | C | C | 90 | C | C | C | C | C | C | — | — | — | — | — |
| | 0.0701 | 0 | 0 | 25 | 0 | 40 | 50 | 50 | — | 45 | 40 | 65 | 90 | 10 | 70 | 95 | 99 | C | 99 | C | — | — | — | — | — |

TABLE B-continued

Herbicide Secondary Preemergence

| CP No. | Rate kg/ha | Sobe | Cotz | Rape | Cbu | Wib | Mogl | Hese | Cie | Vle | Whe | Rcz | Gro | Con | Dbr | Pmi | Byg | Lact | Gft | Ccw | Anbg | Baz | Ruth | Sej | Wob | Cbs | Blgr |
|---|---|---|---|---|---|---|---|---|---|---|---|---|---|---|---|---|---|---|---|---|---|---|---|---|---|---|---|
|  | 0.0175 | 25 | 0 | 0 | 0 | 30 | 0 | 0 | — | 0 | 15 | 0 | 55 | 10 | 25 | 99 | 90 | 90 | 95 | 50 | — | — | — | — | — | — | — |
|  | 0.0087 | 10 | 0 | 0 | 0 | 10 | 0 | 0 | — | 30 | 15 | 10 | 35 | 20 | 0 | 20 | 85 | 90 | 85 | 50 | — | — | — | — | — | — | — |
| 10 | 5.6050 | 95 | 90 | C | 90 | C | C | C | — | C | C | C | C | 99 | C | C | C | C | C | C | — | — | — | — | — | — | — |
|  | 1.1210 | 90 | 0 | C | 90 | C | 95 | 95 | — | 95 | C | 98 | C | 90 | C | C | C | C | C | C | — | — | — | — | — | — | — |
|  | 0.2803 | 90 | N | 95 | 20 | C | 90 | 90 | — | 95 | 90 | 70 | C | 90 | 98 | C | C | C | C | C | — | — | — | — | — | — | — |
|  | 0.0701 | 45 | 10 | 70 | 0 | 95 | 60 | 95 | — | 95 | 70 | 35 | 95 | 80 | 90 | C | C | C | C | C | — | — | — | — | — | — | — |
|  | 0.0175 | 0 | 25 | 45 | 0 | 55 | 50 | 0 | — | 70 | 0 | 45 | 50 | 10 | 60 | 60 | 90 | C | 95 | 95 | — | — | — | — | — | — | — |
|  | 0.0044 | 10 | 0 | 0 | 0 | 70 | 30 | 10 | — | 45 | 10 | 0 | 60 | 5 | 40 | 75 | 90 | C | 95 | C | — | — | — | — | — | — | — |
| 11 | 5.6050 | 20 | 0 | 0 | 35 | 70 | 0 | 0 | — | 0 | 25 | 0 | 25 | 5 | 0 | 10 | 90 | C | 98 | 85 | — | — | — | — | — | — | — |
|  | 1.1210 | 20 | 0 | 0 | 20 | 0 | 0 | 25 | — | 20 | 0 | 0 | 0 | 10 | 0 | 0 | 0 | 20 | 20 | 30 | — | — | — | — | — | — | — |
|  | 0.2803 | 0 | 0 | 0 | 0 | 0 | 0 | 0 | — | 0 | 0 | 0 | 0 | 0 | 0 | 0 | 0 | 0 | 0 | 0 | — | — | — | — | — | — | — |
| 12 | 5.6050 | 0 | 0 | 0 | 0 | 60 | 0 | 0 | — | 0 | 0 | 0 | 0 | 0 | 40 | 0 | 0 | 90 | 20 | 90 | — | — | — | — | — | — | — |
|  | 1.1210 | 0 | 0 | 0 | 0 | 0 | 0 | 0 | — | 0 | 0 | 0 | 0 | 0 | 0 | 0 | 0 | 0 | 0 | 30 | — | — | — | — | — | — | — |
|  | 0.2803 | 0 | 0 | 0 | 0 | 0 | 0 | 0 | — | 0 | 0 | 0 | 0 | 0 | 0 | 0 | 0 | 0 | 0 | 0 | — | — | — | — | — | — | — |
| 13 | 5.6050 | 90 | 60 | 80 | 0 | C | 80 | 80 | — | 90 | C | C | C | 95 | C | C | C | C | C | C | — | — | — | — | — | — | — |
|  | 1.1210 | 70 | 10 | 60 | 0 | 95 | 55 | 70 | — | 80 | 95 | 90 | C | 95 | 90 | C | C | C | C | C | — | — | — | — | — | — | — |
|  | 0.2803 | 30 | 0 | 60 | 0 | 35 | 30 | 0 | — | 0 | 60 | 90 | 98 | 70 | 60 | 95 | 98 | 95 | 98 | 90 | — | — | — | — | — | — | — |
|  | 0.0701 | 10 | 0 | 0 | 0 | 0 | 0 | 0 | — | 0 | 30 | 40 | 90 | 10 | 40 | 90 | 95 | 98 | 95 | 0 | — | — | — | — | — | — | — |
|  | 0.0175 | 30 | 0 | 35 | 0 | 0 | 0 | 0 | — | 0 | 10 | 0 | 0 | N | 30 | 0 | 20 | 95 | 70 | 25 | — | — | — | — | — | — | — |
|  | 0.0087 | N | 0 | N | N | 0 | N | 0 | — | 0 | N | 0 | N | N | 0 | 0 | N | 25 | N | 0 | — | — | — | — | — | — | — |
| 14 | 5.6050 | 95 | 60 | 90 | 0 | C | 80 | 95 | — | 98 | C | C | C | C | C | C | C | C | C | C | — | — | — | — | — | — | — |
|  | 1.1210 | 95 | 35 | 60 | 0 | C | 90 | 80 | — | 90 | C | 95 | C | 98 | C | C | C | C | C | C | — | — | — | — | — | — | — |
|  | 0.2803 | 90 | 20 | 75 | 0 | C | 90 | 60 | — | 80 | 90 | 98 | C | 95 | 90 | C | C | C | C | C | — | — | — | — | — | — | — |
|  | 0.0701 | 25 | 15 | 0 | 0 | 85 | 0 | 10 | — | 20 | 75 | 20 | 95 | 50 | 70 | 95 | C | C | 95 | C | — | — | — | — | — | — | — |
|  | 0.0175 | 10 | 25 | 0 | 10 | 55 | 0 | 0 | — | 30 | 45 | 35 | 90 | 5 | 20 | 70 | 90 | C | 95 | 75 | — | — | — | — | — | — | — |
|  | 0.0087 | 10 | 0 | 0 | 0 | 0 | 0 | 0 | — | 0 | 0 | 10 | 40 | 20 | 0 | 0 | 70 | 85 | 75 | 20 | — | — | — | — | — | — | — |
| 15 | 5.6050 | 45 | 15 | 80 | 0 | 90 | 75 | 90 | — | 90 | C | 95 | C | 95 | C | C | C | C | C | 95 | — | — | — | — | — | — | — |
|  | 1.1210 | 5 | 15 | 25 | 0 | 75 | 0 | 15 | — | 45 | 70 | 20 | 95 | 45 | 65 | 95 | 95 | C | 95 | 98 | — | — | — | — | — | — | — |
|  | 0.2803 | 0 | 25 | 30 | 0 | 45 | 0 | 40 | — | 15 | 40 | 35 | 75 | 25 | 60 | 70 | 50 | 85 | 65 | 35 | — | — | — | — | — | — | — |
|  | 0.0701 | 35 | 10 | 0 | 10 | 0 | 0 | 10 | — | 0 | 15 | 20 | 0 | 0 | 0 | 0 | 0 | 85 | 30 | 0 | — | — | — | — | — | — | — |
|  | 0.0175 | 0 | 0 | 0 | 0 | 0 | 0 | 0 | — | 0 | 15 | 0 | 0 | 0 | 0 | 0 | 0 | 0 | 0 | 0 | — | — | — | — | — | — | — |
|  | 0.0087 | 0 | 0 | 0 | 0 | 0 | 0 | 0 | — | 0 | 0 | 0 | 0 | 0 | 0 | 0 | 0 | 0 | 0 | 0 | — | — | — | — | — | — | — |
| 16 | 5.6050 | 95 | 60 | C | 55 | C | 95 | 90 | — | 90 | C | C | C | C | C | C | C | C | C | C | — | — | — | — | — | — | — |
|  | 1.1210 | 90 | 35 | 95 | 0 | C | 90 | 90 | — | 90 | C | C | C | 95 | C | C | C | C | C | C | — | — | — | — | — | — | — |
|  | 0.2803 | 50 | 20 | 90 | 0 | C | 30 | 55 | — | 70 | 95 | C | C | 95 | C | C | C | C | C | 90 | — | — | — | — | — | — | — |
|  | 0.0701 | 25 | 0 | 40 | 0 | 60 | 0 | 0 | — | 20 | 45 | 95 | 90 | 10 | 75 | C | 95 | C | 95 | 35 | — | — | — | — | — | — | — |
|  | 0.0175 | 0 | 0 | 0 | 0 | 0 | 0 | 0 | — | 0 | 50 | 45 | 70 | 0 | 0 | 35 | 90 | 85 | 95 | 0 | — | — | — | — | — | — | — |
|  | 0.0044 | 0 | 0 | 0 | 0 | 0 | 0 | 0 | — | 0 | 0 | 30 | 0 | 0 | 0 | 0 | 0 | 0 | 75 | 0 | — | — | — | — | — | — | — |
| 17 | 5.6050 | 90 | 70 | 95 | 90 | C | 95 | 90 | — | 90 | C | C | C | 95 | C | C | C | C | C | C | — | — | — | — | — | — | — |
|  | 1.1210 | 80 | 35 | 90 | 10 | 30 | 80 | 85 | — | 90 | 90 | C | 95 | 80 | 90 | C | C | C | C | C | — | — | — | — | — | — | — |
|  | 0.2803 | 45 | N | 70 | 25 | N | 35 | 70 | — | 55 | 45 | 90 | 75 | 40 | 90 | C | C | C | 95 | 90 | — | — | — | — | — | — | — |
|  | 0.0701 | 10 | 35 | 35 | 0 | 0 | 30 | 0 | — | 0 | 10 | 35 | 10 | 0 | 15 | 65 | 90 | 80 | 90 | 0 | — | — | — | — | — | — | — |
|  | 0.0175 | N | 30 | 15 | 0 | N | 20 | N | — | 25 | 0 | N | 0 | 0 | 0 | 30 | 25 | 60 | 35 | N | — | — | — | — | — | — | — |
|  | 0.0087 | 10 | 10 | 25 | 0 | 0 | 0 | 0 | — | 10 | 0 | 0 | 0 | 20 | 0 | 0 | 0 | 0 | 0 | 0 | — | — | — | — | — | — | — |
| 18 | 5.6050 | 95 | 90 | 95 | 85 | C | 95 | 90 | — | 95 | C | C | C | C | C | C | C | C | C | C | — | — | — | — | — | — | — |
|  | 1.1210 | 90 | 65 | 95 | 30 | C | 95 | 90 | — | 90 | C | C | C | 95 | C | C | C | C | C | C | — | — | — | — | — | — | — |
|  | 0.2803 | 65 | 25 | 80 | 20 | 75 | 40 | 40 | — | 60 | 70 | 90 | 95 | 90 | 70 | C | 95 | C | C | 85 | — | — | — | — | — | — | — |
|  | 0.0701 | 15 | 55 | 65 | 20 | 60 | 10 | 45 | — | 50 | 30 | 90 | 40 | 10 | 85 | 95 | 90 | 85 | 90 | 0 | — | — | — | — | — | — | — |
|  | 0.0175 | 0 | 25 | 0 | 0 | 0 | 0 | 0 | — | 30 | 5 | 60 | 0 | 0 | 0 | 80 | 55 | 90 | 45 | 30 | — | — | — | — | — | — | — |
|  | 0.0044 | 10 | 15 | 10 | 0 | 0 | 0 | 0 | — | 10 | 10 | 30 | 0 | 0 | 0 | 45 | 0 | 0 | 15 | 0 | — | — | — | — | — | — | — |
| 19 | 5.6050 | 15 | 55 | 20 | 0 | 80 | 0 | 65 | — | 45 | 0 | 65 | 0 | 10 | 40 | 90 | 15 | C | 30 | 55 | — | — | — | — | — | — | — |
|  | 1.1210 | 15 | 35 | 25 | 15 | 50 | 10 | 0 | — | 30 | 10 | 60 | 0 | N | 25 | 55 | 0 | 60 | 10 | 10 | — | — | — | — | — | — | — |
|  | 0.2803 | N | 30 | 35 | 0 | N | 0 | 10 | — | 45 | 0 | 70 | 0 | 0 | 0 | 50 | 0 | 10 | 0 | N | — | — | — | — | — | — | — |
| 20 | 5.6050 | 90 | 60 | 90 | 40 | C | 90 | 90 | — | 90 | 90 | C | 95 | 90 | C | C | C | C | C | C | — | — | — | — | — | — | — |
|  | 1.1210 | 40 | 50 | 85 | 0 | 90 | 75 | 70 | — | 70 | 70 | C | 95 | 80 | 90 | C | C | C | C | C | — | — | — | — | — | — | — |
|  | 0.2803 | 55 | 25 | 80 | 35 | 45 | 40 | 0 | — | 30 | 20 | 75 | 40 | 15 | 15 | 85 | 90 | C | 90 | 95 | — | — | — | — | — | — | — |
|  | 0.0701 | 15 | 40 | 10 | 0 | N | 0 | N | — | 35 | 10 | 85 | 0 | 0 | 25 | 70 | 35 | 90 | 20 | 80 | — | — | — | — | — | — | — |
| 21 | 5.6050 | 60 | 25 | 95 | N | 90 | 75 | — | — | 70 | 50 | 70 | — | 75 | 90 | — | C | C | C | C | C | 20 | 15 | C | 90 | — | — |
|  | 1.1210 | 5 | 0 | 55 | N | 15 | 30 | — | — | 0 | 15 | 20 | — | 5 | 30 | — | 90 | 99 | C | 99 | 99 | 0 | 10 | 60 | 90 | — | — |
|  | 0.2803 | 0 | 0 | 10 | N | 0 | 0 | — | — | 0 | 0 | 0 | — | 0 | 0 | — | 25 | 95 | 60 | 15 | 15 | 0 | 0 | 40 | 00 | — | — |
|  | 0701 | 10 | 0 | 0 | N | N | 10 | — | — | 0 | 0 | 20 | — | 0 | 0 | — | 0 | 25 | 0 | N | 0 | 0 | N | 20 | 0 | — | — |
| 22 | 5.6050 | 65 | 0 | 80 | N | 90 | 25 | — | — | 70 | C | 75 | 75 | C | — | C | C | C | 99 | C |  | 30 | 10 | C | C | — | — |
|  | 1.1210 | 5 | 0 | 25 | N | 20 | 0 | — | — | 30 | 25 | 50 | — | 25 | 75 | — | 95 | C | C | 60 | C | 10 | 0 | 95 | 90 | — | — |
|  | 0.2803 | 0 | 0 | 0 | N | 0 | 0 | — | — | 20 | 0 | 0 | — | 0 | 0 | — | 5 | 80 | 10 | 10 | 0 | 0 | 0 | 30 | 15 | — | — |
|  | 0.0701 | N | N | 0 | N | 0 | N | — | — | N | 0 | 0 | — | 0 | 0 | — | N | 0 | 0 | 0 | 0 | 0 | 0 | 0 | 0 | — | — |
|  | 0.0175 | 0 | 0 | 0 | N | 0 | 0 | — | — | 0 | 0 | N | — | 0 | 0 | — | 25 | 70 | 0 | 0 | 0 | 0 | 0 | 0 | 0 | — | — |
| 23 | 5.6050 | 0 | 0 | 80 | 0 | 20 | 25 | — | — | 0 | 30 | 50 | — | 30 | 50 | — | 98 | C | 98 | 90 | C | 0 | 0 | 98 | 80 | — | — |
|  | 1.1210 | 0 | 0 | 0 | 0 | 10 | 40 | — | — | 0 | 0 | 30 | — | 0 | 0 | — | 0 | 60 | 20 | 0 | 50 | 0 | 0 | 40 | 0 | — | — |
|  | 0.2803 | 0 | 0 | 0 | 0 | 0 | 25 | — | — | 0 | 0 | 0 | — | 5 | 0 | — | 20 | 0 | 0 | 0 | 10 | 0 | 0 | 0 | 0 | — | — |
|  | 0.0701 | 0 | 0 | 0 | 0 | 0 | 0 | — | — | 0 | 0 | 5 | — | 0 | 0 | — | 25 | 0 | 0 | 0 | 0 | 0 | 0 | 0 | 0 | — | — |
| 24 | 5.6050 | 95 | 75 | C | 75 | 99 | 98 | — | — | 98 | C | C | — | 99 | C | — | C | C | C | C | C | 95 | 80 | C | C | — | — |
|  | 1.1210 | 80 | 25 | 98 | 30 | C | 98 | — | — | 90 | 98 | C | — | 98 | C | — | C | C | C | C | C | 60 | 75 | C | C | — | — |
|  | 0.2803 | 65 | 5 | 95 | 10 | C | 95 | — | — | 75 | 95 | C | — | 65 | 95 | — | C | C | C | C | C | 25 | 30 | C | 99 | — | — |
|  | 0.0701 | 0 | 0 | 75 | 0 | 98 | 60 | — | — | 0 | 80 | 50 | — | 20 | 80 | — | C | C | C | 98 | C | 20 | 10 | C | 90 | — | — |
|  | 0.0175 | 0 | 0 | 60 | 0 | 85 | 25 | — | — | 0 | 60 | 20 | — | 5 | 70 | — | 80 | C | 99 | 90 | C | 0 | 0 | 65 | 80 | — | — |
|  | 0.0044 | 0 | 0 | 0 | 0 | 0 | 0 | — | — | 0 | 0 | 0 | — | 0 | 0 | — | 30 | C | 55 | 0 | 60 | 0 | 0 | 50 | 30 | — | — |

TABLE B-continued

| | | Herbicide Secondary Preemergence | | | | | | | | | | | | | | | | | | | | | | | | |
|---|---|---|---|---|---|---|---|---|---|---|---|---|---|---|---|---|---|---|---|---|---|---|---|---|---|---|
| CP No. | Rate kg/ha | S o b e | C o t z | R a p e | C o b u | W i l w | M o g l | H e e | C i w e e | V e l z e | W h e z | R i r o e | G r o s r | C o r b | D o b r | P r m i | B y g r | L a r g | G r c t | C o c b | A n n w g | B a u r z | R u r t h | S e j g | W i o a | C w b s | B l g r |
|---|---|---|---|---|---|---|---|---|---|---|---|---|---|---|---|---|---|---|---|---|---|---|---|---|---|---|
| 25 | 5.6050 | 80 | 50 | 99 | 0 | C | 98 | — | — | 99 | C | C | — | 98 | C | — | C | C | C | C | C | 80 | 90 | C | C | — | — |
| | 1.1210 | 25 | 20 | 98 | 0 | C | 80 | — | — | 95 | 99 | 80 | — | 50 | 99 | — | C | C | C | C | C | 30 | 60 | C | 99 | — | — |
| | 0.2803 | 0 | 0 | 85 | 0 | 95 | 30 | — | — | 50 | 80 | 50 | — | 25 | 95 | — | C | C | C | C | C | 15 | 30 | 99 | 95 | — | — |
| | 0.0701 | 0 | 0 | 10 | 0 | 10 | 0 | — | — | 0 | 30 | 20 | — | 5 | 60 | — | 70 | 80 | 20 | 20 | 0 | 10 | 10 | 50 | 10 | — | — |
| | 0.0175 | 0 | 0 | 0 | 0 | 0 | 0 | — | — | 0 | 10 | 0 | — | 10 | 0 | — | 0 | 0 | 15 | 70 | 10 | 0 | 0 | 0 | 0 | — | — |
| | 0.0044 | 0 | 0 | 0 | 0 | 0 | 0 | — | — | 0 | 0 | 0 | — | 0 | 0 | — | 0 | 0 | 0 | 0 | 10 | 0 | 0 | 0 | 0 | — | — |
| 26 | 5.6050 | 99 | 80 | 99 | 75 | C | C | — | — | 99 | C | C | — | C | C | — | C | C | C | C | C | C | 95 | C | C | — | — |
| | 1.1210 | 95 | 70 | 95 | 70 | C | C | — | — | 99 | C | C | — | C | 98 | — | C | C | C | C | C | 70 | 80 | C | 98 | — | — |
| | 0.2803 | 75 | 50 | 95 | 30 | C | 70 | — | — | 95 | C | C | — | 95 | 95 | — | C | C | C | C | C | 25 | 20 | C | C | — | — |
| | 0.0701 | 40 | 0 | 90 | 0 | 90 | 30 | — | — | 75 | 70 | 90 | — | 25 | 90 | — | C | C | C | C | C | 20 | 10 | C | 95 | — | — |
| | 0.0175 | 25 | 0 | 35 | 0 | 70 | 20 | — | — | 25 | 30 | 40 | — | 20 | 30 | — | 99 | 99 | 98 | 80 | C | 0 | 0 | 99 | 80 | — | — |
| | 0.0044 | 0 | 0 | 0 | 0 | 0 | 0 | — | — | 0 | 0 | 0 | — | 5 | 0 | — | 50 | 90 | 80 | 0 | 90 | 0 | 0 | 75 | 70 | — | — |
| 27 | 5.6050 | C | 95 | C | 70 | C | C | — | — | C | C | C | — | C | 99 | — | C | C | C | C | C | 85 | 98 | C | 98 | — | — |
| | 1.1210 | 95 | 40 | 98 | 0 | C | 95 | — | — | 99 | C | C | — | 98 | 95 | — | C | C | C | C | C | 60 | 80 | C | C | — | — |
| | 0.2803 | 30 | 20 | 95 | 0 | 99 | 65 | — | — | 90 | 95 | 98 | — | 30 | 95 | — | C | C | C | C | C | 20 | 20 | C | 98 | — | — |
| | 0.0701 | 0 | 0 | 55 | 0 | 80 | 60 | — | — | 30 | 40 | 99 | — | 25 | 60 | — | C | C | C | C | C | 0 | 0 | C | 80 | — | — |
| | 0.0175 | 5 | 0 | 0 | 0 | 30 | 0 | — | — | 0 | 0 | 30 | — | 0 | 0 | — | 95 | 95 | 90 | 20 | 99 | 0 | 0 | 80 | 20 | — | — |
| | 0.0044 | 0 | 0 | 0 | 0 | 0 | 0 | — | — | 0 | 0 | 10 | — | 0 | 10 | — | 0 | 25 | 10 | 0 | 0 | 0 | 0 | 30 | 0 | — | — |
| 28 | 5.6050 | 95 | 10 | 90 | 0 | 95 | C | — | — | 95 | 30 | 95 | — | 95 | 80 | — | C | C | C | C | C | 0 | 60 | C | 95 | — | — |
| | 1.1210 | 40 | 0 | 0 | 0 | 70 | 70 | — | — | 25 | 10 | 50 | — | 25 | 10 | — | 99 | C | 95 | C | 90 | 0 | 10 | 99 | 80 | — | — |
| | 0.2803 | 0 | 0 | 0 | 0 | 0 | 0 | — | — | 0 | 0 | 10 | — | 5 | 0 | — | 0 | 98 | 70 | 98 | 0 | 0 | 0 | 80 | 0 | — | — |
| | 0.0701 | 0 | 0 | 0 | 0 | 0 | 0 | — | — | 0 | 0 | 0 | — | 0 | 0 | — | 0 | 5 | 0 | 20 | 0 | 0 | 0 | 65 | 0 | — | — |
| 29 | 5.6050 | 80 | 0 | 95 | 0 | C | 35 | — | — | 95 | C | 99 | — | C | C | — | C | C | C | C | C | 10 | 30 | C | C | — | — |
| | 1.1210 | 0 | 0 | 40 | 0 | 95 | 0 | — | — | 50 | 99 | 60 | — | 60 | C | — | C | C | C | C | C | 0 | 20 | C | 99 | — | — |
| | 0.2803 | 5 | 0 | 25 | 0 | 15 | 0 | — | — | 20 | 0 | 0 | — | 0 | 15 | — | 95 | 80 | 10 | 10 | 95 | 0 | 0 | 99 | 90 | — | — |
| | 0.0701 | 0 | 0 | 10 | 0 | 0 | 0 | — | — | 0 | 0 | 0 | — | 0 | 0 | — | 0 | 0 | 10 | 15 | 0 | 0 | 10 | 00 | 15 | — | — |
| | 0.0175 | 0 | 0 | 10 | 0 | 0 | 0 | — | — | 0 | 0 | 0 | — | 0 | 0 | — | 0 | 0 | 0 | 0 | 0 | 0 | 0 | 0 | 0 | — | — |
| 30 | 5.6050 | 80 | 40 | 99 | 50 | C | 98 | — | — | C | C | C | — | 95 | C | — | C | C | C | C | C | 80 | 75 | C | C | — | — |
| | 1.1210 | 75 | 10 | 98 | 0 | C | 90 | — | — | 80 | 99 | C | — | 95 | 98 | — | C | C | C | C | C | 65 | 60 | C | 99 | — | — |
| | 0.2803 | 0 | 0 | 75 | 0 | 75 | 0 | — | — | 0 | 98 | 60 | — | 25 | 75 | — | C | C | C | 50 | C | 25 | 0 | 98 | 98 | — | — |
| | 0.0701 | 0 | 0 | 25 | 0 | 75 | 0 | — | — | 0 | 40 | 0 | — | 20 | 60 | — | 98 | 99 | 99 | 25 | C | 0 | 0 | 70 | 90 | — | — |
| | 0.0175 | 0 | 0 | 0 | 0 | 0 | 0 | — | — | 0 | 0 | 0 | — | 0 | 0 | — | 20 | 75 | 0 | 0 | 60 | 0 | 0 | 30 | 0 | — | — |
| 31 | 5.6050 | 0 | 0 | 35 | 0 | 40 | 5 | — | — | 0 | 15 | 25 | — | 0 | 60 | — | 90 | 99 | 98 | 30 | C | 0 | 60 | 70 | 80 | — | — |
| | 1.1210 | 0 | 0 | 0 | 0 | 50 | 0 | — | — | 0 | 0 | 0 | — | 10 | 10 | — | 0 | 0 | 30 | 60 | 20 | 0 | 20 | 0 | 0 | — | — |
| | 0.2803 | 0 | 0 | 0 | 0 | 20 | 0 | — | — | 0 | 0 | 0 | — | 0 | 5 | — | 0 | 0 | 0 | 20 | 0 | 0 | 0 | 0 | 0 | — | — |
| 32 | 5.6050 | 99 | 75 | C | 70 | C | 99 | — | — | 99 | C | C | — | C | C | — | C | C | C | C | C | C | C | C | C | — | — |
| | 1.1210 | 90 | 20 | 99 | 20 | C | 95 | — | — | 95 | C | C | — | C | C | — | C | C | C | C | C | 95 | C | C | C | — | — |
| | 0.2803 | 75 | 10 | 95 | 0 | C | 70 | — | — | 80 | C | 95 | — | 80 | C | — | C | C | C | C | C | 85 | 60 | C | 95 | — | — |
| | 0.0701 | 10 | 0 | 85 | 0 | 98 | 30 | — | — | 30 | 95 | 50 | — | 25 | 98 | — | C | C | C | 90 | C | 35 | 30 | 99 | 95 | — | — |
| | 0.0175 | 0 | 0 | 60 | 0 | 85 | 25 | — | — | 0 | 50 | 25 | — | 10 | 80 | — | 98 | 98 | 95 | 70 | C | 20 | 10 | 90 | 90 | — | — |
| | 0.0044 | 0 | 0 | 55 | 0 | 50 | 0 | — | — | 0 | 20 | 30 | — | 5 | 20 | — | 40 | 95 | 80 | 30 | 80 | 0 | 20 | 50 | 70 | — | — |
| 33 | 5.6050 | 0 | 0 | 95 | 0 | C | 95 | — | — | 30 | C | 95 | — | 40 | 99 | — | C | C | C | C | — | — | 85 | C | 95 | 99 | C |
| | 1.1210 | 0 | 0 | 90 | 0 | C | 80 | — | — | 40 | 90 | 75 | — | 40 | 85 | — | C | C | C | C | — | — | 65 | 99 | 90 | 90 | C |
| | 0.2803 | 0 | 0 | 10 | 0 | 65 | 0 | — | — | 0 | 10 | 0 | — | 0 | 20 | — | 95 | 95 | 90 | 70 | — | — | 65 | 80 | 85 | 85 | 90 |
| | 0.0701 | 0 | 0 | 0 | 0 | N | 0 | — | — | 0 | 0 | 0 | — | 0 | 0 | — | 0 | 0 | 90 | 45 | — | — | N | 0 | 15 | 65 | 75 |
| | 0.0175 | 0 | 0 | 0 | 0 | 0 | 0 | — | — | 0 | 0 | 0 | — | 0 | 0 | — | 0 | 0 | 10 | 0 | — | — | 35 | 0 | 10 | 25 | 45 |
| | 0.0044 | 0 | 0 | 0 | 0 | 0 | 0 | — | — | 0 | 0 | 0 | — | 0 | 0 | — | 0 | 0 | 0 | 0 | — | — | 0 | 0 | 0 | 0 | 30 |
| 34 | 5.6050 | 0 | 0 | 20 | 0 | 20 | 0 | — | — | 0 | 15 | 0 | — | 5 | 30 | — | 50 | 99 | 90 | 50 | 60 | 20 | 10 | — | 15 | — | — |
| | 1.1210 | 0 | 0 | 25 | 0 | 0 | 0 | — | — | 0 | 0 | 0 | — | 0 | 0 | — | 0 | 25 | 15 | — | 10 | 15 | 0 | 0 | 0 | — | — |
| 35 | 5.6050 | 95 | 60 | 98 | 20 | 99 | 98 | — | — | 99 | C | C | — | C | C | — | C | C | C | C | C | 98 | 90 | C | C | — | — |
| | 1.1210 | 75 | 0 | 95 | 0 | 99 | 75 | — | — | 95 | C | C | — | 99 | C | — | C | C | C | C | C | 95 | 60 | C | C | — | — |
| | 0.2803 | 10 | 5 | 85 | 0 | 95 | 60 | — | — | 80 | 95 | 75 | — | 90 | 95 | — | C | C | C | 95 | C | 70 | 40 | C | 95 | — | — |
| | 0.0701 | 0 | 0 | 10 | 0 | 60 | 0 | — | — | 0 | 70 | 30 | — | 20 | 85 | — | 99 | C | 98 | 55 | C | 25 | 30 | 95 | 95 | — | — |
| | 0.0175 | 0 | 0 | 0 | 0 | 10 | 0 | — | — | 0 | 20 | 0 | — | 0 | 40 | — | 70 | 95 | 60 | 10 | 95 | 15 | 10 | 65 | 60 | — | — |
| | 0.0044 | 0 | 0 | 0 | 0 | 0 | 0 | — | — | 0 | 0 | 0 | — | 0 | 0 | — | 0 | 0 | 15 | 0 | 0 | 0 | 0 | 0 | 0 | — | — |
| 37 | 5.6050 | 95 | 0 | 99 | 0 | 98 | 95 | — | — | 98 | C | C | — | 99 | 99 | — | C | C | C | C | C | 60 | 99 | — | C | — | — |
| | 1.1210 | 0 | 0 | 99 | 0 | C | 70 | — | — | 90 | C | 98 | — | 70 | 95 | — | C | C | C | C | C | 50 | 20 | C | 98 | — | — |
| | 0.2803 | 0 | 0 | 80 | 0 | 90 | 0 | — | — | 0 | 65 | 30 | — | 25 | 60 | — | 99 | C | 90 | C | 15 | 20 | C | 80 | — | — | — |
| | 0.0701 | 0 | 0 | 60 | 0 | 60 | 0 | — | — | 0 | 25 | 10 | — | 0 | 60 | — | 95 | 99 | 90 | 30 | C | 0 | 0 | 80 | 75 | — | — |
| | 0.0175 | 0 | 0 | 0 | 0 | 35 | 0 | — | — | 0 | 0 | 0 | — | 0 | 0 | — | 0 | 60 | 75 | 20 | 85 | 0 | 0 | 40 | 0 | — | — |
| | 0.0044 | 0 | 0 | 0 | 0 | 20 | 0 | — | — | 0 | 0 | 10 | — | 0 | 0 | — | 0 | 50 | 0 | 0 | 0 | 0 | 0 | 20 | 0 | — | — |

POST-EMERGENT HERBICIDE ACTIVITY ON PLANTS

Although, as has been stated above, the compounds of this invention exhibit predominantly pre-emergence activity in greenhouse testing, nevertheless many of these compounds are active post-emergent herbicides. The post-emergent activity is best seen on younger plants treated at the 1⅜ to 2 leaf stage. In the tests which follow, larger and more developed plants were used.

The post-emergence herbicidal activity of compounds of this invention was demonstrated by greenhouse testing, and the results are shown in the following Table C. The post-emergent herbicidal activity data in Table C are based on the percent plant control of each tested plant species. The term "C" designates complete control.

Top soil was placed in pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species were placed on the soil and pressed into the soil surface. The seeds and/or vegetative propagules were covered with soil and leveled. The pans were then placed on a bench in the greenhouse and watered as needed for germination and growth. After the plants reached the desired age (two to three weeks), each pan (except the control pans) was moved to a spraying chamber and sprayed by means of an atomizer. The spray solution or suspension contained about 0.4% by volume of an emulsifying agent and a sufficient amount of the candidate chemical to give an application rate of the active ingredient of 11.2 kg/ha while applying a total amount of solution or suspension equivalent to 1870 L/ha. The pans were returned to the greenhouse and watered as before and the injury to the plants as compared to those in control pans was observed at approximately 10–14 days (usually 11 days). The plant identifying codes in Table C are the same as above defined.

TABLE C

| CP No. | Rate kg/ha | Yens | Abjg | Sejgr | Dobr | Bygr | Mogl | Cobu | Vele | Inmu | Wibw |
|---|---|---|---|---|---|---|---|---|---|---|---|
| 1 | 11.21 | 0 | 0 | 30 | 0 | 0 | 0 | 0 | 0 | 20 | 0 |
| 2 | 11.21 | 0 | 0 | 10 | 0 | 0 | 10 | 0 | 10 | 0 | 0 |
| 3 | 11.21 | 0 | 0 | 0 | 0 | 0 | 0 | 30 | 0 | 20 | 0 |
| 4 | 11.21 | 0 | 0 | 0 | 0 | 0 | 10 | 0 | 0 | 0 | 0 |
| 5 | 11.21 | 0 | 0 | 60 | 10 | 0 | 20 | 0 | 0 | 50 | 0 |
| 6 | 11.21 | 0 | 0 | 0 | 0 | 0 | 10 | 0 | 0 | 0 | 0 |
| 7 | 11.21 | 0 | 0 | 30 | 0 | 0 | 0 | 10 | 0 | 10 | 10 |
| 8 | 11.21 | 0 | 0 | 0 | 0 | 0 | 10 | 20 | 0 | 30 | 10 |
| 9 | 11.21 | 0 | 0 | 0 | 0 | 20 | 20 | 10 | 0 | 10 | 10 |
| 10 | 11.21 | 0 | 0 | 10 | 0 | 20 | 0 | 0 | 0 | 0 | 10 |
| 11 | 11.21 | 0 | 0 | 0 | 0 | 0 | 10 | 0 | 0 | 30 | 0 |
| 12 | 11.21 | 0 | 0 | 0 | 0 | 0 | 20 | 0 | 0 | 0 | 0 |
| 13 | 11.21 | 10 | 20 | 70 | 10 | 60 | 50 | 30 | 20 | 60 | 50 |
| 14 | 11.21 | 0 | 20 | 40 | 10 | 50 | 50 | 30 | 20 | 60 | 70 |
| 15 | 11.21 | 0 | 0 | 40 | 0 | 30 | 40 | 20 | 20 | 40 | 40 |
| 16 | 11.21 | 0 | 20 | 60 | 0 | 50 | 50 | 50 | 40 | 50 | 70 |
| 17 | 11.21 | 0 | 0 | 0 | 0 | 50 | 50 | 40 | 70 | 60 | 60 |
| 18 | 11.21 | 0 | 0 | 0 | 60 | 60 | 50 | 40 | 70 | 70 | 70 |
| 19 | 11.21 | 0 | 0 | 0 | 0 | 30 | 10 | 10 | 0 | — | 0 |
| 20 | 11.21 | 0 | 0 | 0 | 0 | 0 | 30 | 0 | 30 | 50 | 50 |
| 21 | 11.21 | 10 | 30 | 0 | 10 | 10 | 20 | 30 | 0 | 20 | 10 |
| 22 | 11.21 | 0 | 0 | 0 | 0 | 0 | 10 | 20 | 20 | 10 | 0 |
| 23 | 11.21 | 0 | 0 | 0 | 0 | 0 | 10 | 10 | 0 | 0 | 0 |
| 24 | 11.21 | 0 | 0 | 30 | 0 | 30 | 20 | 30 | 30 | 30 | 30 |
| 25 | 11.21 | 0 | 0 | 0 | 0 | 0 | 20 | 20 | 10 | 20 | 10 |
| 26 | 11.21 | 0 | 0 | 10 | 0 | 20 | 20 | 20 | 30 | 30 | 10 |
| 27 | 11.21 | 0 | 0 | 0 | 0 | 10 | 20 | 20 | 10 | — | — |
| 28 | 11.21 | 0 | 0 | 0 | 0 | 0 | 30 | 60 | 20 | 40 | 10 |
| 29 | 11.21 | 0 | 0 | 0 | 0 | 0 | 20 | 0 | 30 | 0 | |
| 30 | 11.21 | 0 | 10 | 50 | 10 | 60 | 50 | 50 | 40 | 30 | 40 |
| 31 | 11.21 | 0 | 30 | 30 | 10 | 0 | 0 | 40 | 0 | 60 | 20 |
| 32 | 11.21 | 0 | 20 | 50 | 20 | 70 | 30 | 40 | 30 | 50 | 40 |
| 33 | 11.21 | 10 | 0 | 30 | 0 | 0 | 50 | 20 | 30 | 30 | 50 |
| 34 | 11.21 | 0 | 0 | 20 | 0 | 10 | 30 | 20 | 20 | 30 | 0 |
| 35 | 11.21 | 0 | 0 | 50 | 10 | 10 | 40 | 30 | N | 40 | 50 |
| 36 | 11.21 | 10 | 20 | 0 | 10 | 20 | 0 | 10 | 20 | 40 | 30 |
| 37 | 11.21 | 0 | 10 | 30 | 0 | 30 | 40 | 40 | 30 | 40 | 30 |

Compounds of this invention were also tested for herbicidal activity on weed plants in the presence of crop plants according to the following procedure:

Topsoil (silt loam) is sieved through a screen having 1.27 cm openings. In some of the tests the soil was mixed with fertilizer (1225 g/cu. m of 12/5/9 containing isobutylidene diurea), while in other tests the fertilizer was omitted. This mixture is steam sterilized and then placed in aluminum pans 6.985 cm deep having ten holes in the bottom each 0.635 cm in diameter. The soil mixture is compacted to a depth of 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with 1.27 cm of a mixture of 50% topsoil and 50% of a mixture of Canadian sphagnum peat moss, vermiculite and a wetting agent. The pans are then placed on a capillary mat on a greenhouse bench and subirrigated as needed. After the plants reach the desired stage (9 to 14 days, 1 to 3 true leaf stage), each pan (except the control pans) is removed to a spraying chamber and sprayed by means of an atomizer, operating at a spray pressure of 170.3 kPa (10 psig) at the application rates noted in Table D. In the spray solution is an amount of an emulsifying agent mixture (35% butylamine salt of dodecylbenzenesulfonic acid and 65% tall oil condensed with ethylene oxide in the ratio of 11 mols of ethylene oxide/mol of tall oil) to give a spray solution or suspension. The spray solution or suspension contains a sufficient amount of the candidate chemical in order to give application rates of the active ingredient corresponding to those shown in Table D below while applying a total amount of solution or suspension equivalent to 1870 L/Ha (200 gallons/acre). The pans are returned to the greenhouse and watered as before and the injury to the plants as compared to the control pans is observed at approximately 10–14 days (usually 11 days).

In the following Table D the legends used to identify the plant species are the same as those above.

TABLE D

| CP No. | Rate kg/ha | Sobe | Cotz | Rape | Cobu | Wibw | Migl | Hoge | Vele | Whee | RhCz | Giro | Conr | Dobr | Prmg | Bygr | Lafc | Grft | Cocw |
|---|---|---|---|---|---|---|---|---|---|---|---|---|---|---|---|---|---|---|---|
| 17 | 11.21 | 65 | 35 | 75 | 35 | 80 | 40 | 50 | 40 | 0 | 50 | 0 | 50 | 0 | 0 | 35 | 80 | 35 | 70 |
| | 5.60 | 40 | 30 | 65 | 40 | 10 | 40 | 40 | 35 | 0 | 0 | 0 | 50 | 0 | 0 | 30 | 75 | 40 | 25 |
| | 1.12 | 10 | 25 | 25 | 65 | 30 | 0 | 40 | 30 | 35 | 0 | — | 0 | 20 | 0 | 0 | 0 | 60 | 0 | 0 |
| | 0.28 | 03 | 25 | 30 | 40 | 25 | 10 | 35 | 25 | 25 | 0 | 0 | 0 | 10 | 0 | 0 | 0 | 50 | 0 | 0 |
| 18 | 11.21 | 00 | 60 | 50 | 80 | 50 | 80 | 60 | 65 | 80 | 0 | 20 | 30 | 50 | 5 | 35 | 75 | 80 | 40 | 75 |
| | 5.60 | 50 | 60 | 35 | 80 | 50 | 70 | 50 | 75 | 80 | 0 | 0 | 25 | 50 | 25 | 25 | 10 | 75 | 40 | 50 |
| | 1.12 | 10 | 40 | 40 | 50 | 35 | — | 50 | 50 | 50 | 20 | 20 | 0 | 40 | 0 | 0 | 0 | 75 | 30 | — |
| | 0.28 | 03 | 25 | 25 | 65 | 40 | 0 | 35 | 30 | 30 | 0 | 0 | 25 | 0 | 0 | 0 | 0 | 60 | 35 | 0 |

As can be seen from the data above, some of the compounds appear to be quite safe on certain crops and can thus be used for selective control of weeds in these crops.

The herbicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from above 0.5 to 60 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor or anti-foaming agent or both.

Other formulations include dust concentrates comprising from 0.1 to 60% by weight of the active ingredient on a suitable extender; these dusts may be diluted for application at concentrations within the range of from about 0.1-10% by weight.

Aqueous suspensions or emulsions may be prepared by stirring a nonaqueous solution of a water-insoluble active ingredient and an emulsification agent with water until uniform and then homogenizing to give stable emulsion of very finely-divided particles. The resulting concentrated aqueous suspension is characterized by its extremely small particle size, so that when diluted and sprayed, coverage is very uniform. Suitable concentrations of these formulations contain from about 0.1–60% preferably 5–50% by weight of active ingredient, the upper limit being determined by the solubility limit of active ingredient in the solvent.

Concentrates are usually solutions of active ingredient in water-immiscible or partially water-immiscible solvents together with a surface active agent. Suitable solvents for the active ingredient of this invention include N,-N-dimethylformamide, dimethylsulfoxide, N-methyl-pyrrolidone, hydrocarbons, and water-immiscible ethers, esters, or ketones. However, other high strength liquid concentrates may be formulated by dissolving the active ingredient in a solvent then diluting, e.g., with kerosene, to spray concentration.

The concentrate compositions herein generally contain from about 0.1 to 95 parts (preferably 5–60 parts) active ingredient, about 0.25 to 50 parts (preferably 1–25 parts) surface active agent and where required about 4 to 94 parts solvent, all parts being by weight based on the total weight of emulsifiable oil.

Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite, and vermiculite are examples of operable classes of particulate mineral extenders. The preferred extenders are the porous, absorptive, preformed particles such as preformed and screened particulate attapulgite or heat expanded, particulate vermiculite and the finely-divided clays such as kaolin clays, hydrated attapulgite or bentonitic clays. These extenders are sprayed or blended with the active ingredient to form the herbicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention included, for example, triazines, ureas, carbamates, acetamides, acetanilides, uracils, acetic acid or phenol derivatives, thiolcarbamates, triazoles, benzoic acids, nitriles, biphenyl ethers and the like, such as:

Heterocyclid Nitrogen/Sulfur Derivatives

2-Chloro-4-ethylamino-6-isopropylamino-s-triazine
2-Chloro-4,6-bis(isopropylamino)-s-triazine
2-Chloro-4,6-bis(ethylamino)-s-triazine
3-Isopropyl-1H-2,1,3-benzothiadiazin-4-(3H)-one 2,2 dioxide
3-Amino-1,2,4-triazole
6,7-Dihydrodipyrido(1,2-d:a',1'-c)pyrizidiinium salt
5-Bromo-3-isopropyl-6-methyluracil 1,1'-dimethyl-4,4'-bipyridinium
2-(4-isopropyl-4-methyl-5-oxo-2-imidazolin-2-yl)- 3-quinolinecarboxylic acid
Isopropylamino salt of 2-(4-isopropyl-4-methyl-5- oxo-2-imidazolin-2-yl)nicotinic acid
Methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate Ureas N-(4-chlorophenoxy) phenyl-N,N-dimethylurea
N,N-dimethyl-N'-(3-chloro-4-methylphenyl) urea
3-(3,4-Dichlorophenyl)-1,1-dimethylurea 1,3-Dimethyl-3-(2-benzothiazolyl) urea
3-(p-Chlorophenyl)-1,1-dimethylurea 1-Butyl-3-(3,4-dichlorophenyl)-1-methylurea
2-Chloro-N[(4-methoxy-6-methyl-3,5-triazin-2-yl) aminocarbonyl]-benzenesulfonamide
Methyl 2-(((((4,6-dimethyl-2-pyrimidinyl)amino)-carbonyl)amino)sulfonyl) benzoate
Ethyl 2-[methyl 2-(((((4,6-dimethyl-2-pyrimidinyl)amino)carbonyl)amino)sulfonyl)] benzoate
Methyl-2((4,6-dimethoxy pyrimidin-2-yl)aminocarbonyl)amino sulfonyl methyl) benzoate
Methyl 2-(((((4-methoxy-6-methyl-1,3,5-triazin-2-yl)amino)carbonyl)amino)sulfonyl) benzoate Carbamates/Thiolcarbamates 2-Chloroallyl diethyldithiocarbamate
S-(4-chlorobenzyl)N,N-diethylthiolcarbamate
Isopropyl N-(3-chlorophenyl) carbamate
S-2,3-dichloroallyl N,N-diisopropylthiolcarbamate
S-N,N-dipropylthiolcarbamate
S-propyl N,N-dipropylthiolcarbamate
S-2,3,3-trichloroallyl N,N-diisopropylthiolcarbamate Acetamides/Acetanilides/Anilines/Amides 2-Chloro-N,N-diallylacetamide
N,N-dimethyl-2,2-diphenylacetamide
N-(2,4-dimethyl-5-[[(trifluoromethyl)sulfonyl]amino] phenyl]acetamide N-Isopropyl-2-chloroacetanilide
2',6'-Diethyl-N-methoxymethyl-2-chloroacetanilide
2'-Methyl-6'-ethyl-N-(2-methoxypropyl-2-yl)-2-chloroacetanilide
α,α,α-Trifluoro-2,6-dinitro-N,N-dipropyl-p-toluidine
N-(1,1-dimethylpropynyl)-3,5-dichlorobenzamide Acids/Esters/Alcohols 2,2-Dichloropropionic acid
2-Methyl-4-chlorophenoxyacetic acid
2,4-Dichlorophenoxyacetic acid
Methyl-2-[4-(2,4-dichlorophenoxy)phenoxy]propionate
3-Amino-2,5-dichlorobenzoic acid
2-Methoxy-3,6-dichlorobenzoic acid
2,3,6-Trichlorophenylacetic acid
N-1-naphthylphthalamic acid
Sodium 5-[2-chloro-4-(trifluoromethyl)phenoxy]-2-nitrobenzoate
4,6-Dinitro-o-sec-butylphenol N-(phosphonomethyl) glycine and its salts.
Butyl 2-[4-[(5-(trifluoromethyl)-2-pyridinyl)oxy]-phenoxy]-propanoate Ethers 2,4-Dichlorophenyl-4-nitrophenyl ether
2-Chloro-α,α,α-trifluoro-p-tolyl-3-ethoxy-4-nitrodiphenyl ether
5-(2-chloro-4-trifluoromethylphenoxy)-N-methyl sulfonyl
2-nitrobenzamide
1'-(Carboethoxy) ethyl 5-[2-chloro-4-(trifluoro methyl)-phenoxy]-2-nitrobenzoate Miscellaneous 2,6-Dichlorobenzonitrile
Monosodium acid methanearsonate
Disodium methanearsonate
2-(2-chlorophenyl)methyl-4,4-dimethyl-3-isoxazolidinone
7-oxabicyclo (2.2.1) heptane, 1-methyl-4-(1-methyl ethyl)-2-(2-methylphenylmethoxy)-,exo-
Fertilizers useful in combination with the active ingredients include, for example ammonium nitrate, urea, potash and superphosphate. Other useful additaments include materials in which plant organisms take root and grow such as compost, manure, humus, sand and the like.

Herbicidal formulations of the types described above are exemplified in several illustrative embodiments below.

| | Weight Percent |
|---|---|
| I. Emulsifiable Concentrates | |
| A. Compound of Example No. 2 | 11.0 |
| Free acid of complex organic phosphate or aromatic or aliphatic hydrophobe base (e.g., GAFAC RE-610, registered trademark of GAF Corp.) | 5.59 |
| Polyoxyethylene/polyoxypropylene block copolymer with butanol (e.g., Tergitol XH, registered trademark of Union Carbide Corp.) | 1.11 |
| Phenol | 5.34 |
| Monochlorobenzene | 76.96 |
| | 100.00 |
| B. Compound of Example No. 13 | 25.00 |
| Free acid of complex organic phosphate of aromatic or aliphatic hydrophobe base (e.g., GAFAC RE-610) | 5.00 |
| Polyoxyethylene/polyoxypropylene block copolymer with butanol (e.g., Tergitol XH) | 1.60 |
| Phenol | 4.75 |
| Monochlorobenzene | 63.65 |
| | 100.00 |
| II. Flowables | |
| A. Compound of Example No. 23 | 25.00 |
| Methyl cellulose | 0.3 |
| Silica Aerogel | 1.5 |
| Sodium lignosulfonate | 3.5 |
| Sodium N-methyl-N-oleyl taurate | 2.0 |
| Water | 67.7 |
| | 100.00 |
| B. Compound of Example No. 17 | 45.0 |
| Methyl cellulose | .3 |
| Silica aerogel | 1.5 |
| Sodium lignosulfonate | 3.5 |
| Sodium N-methyl-N-oleyl taurate | 2.0 |
| Water | 47.7 |
| | 100.00 |
| III. Wettable Powders | |
| A. Compound of Example No. 4 | 25.0 |
| Sodium lignosulfonate | 3.0 |
| Sodium N-methyl-N-oleyl-taurate | 1.0 |
| Amorphous silica (synthetic) | 71.0 |
| | 100.00 |
| B. Compound of Example 20 | 80.00 |
| Sodium dioctyl sulfosuccinate | 1.25 |
| Calcium lignosulfonate | 2.75 |
| Amorphous silica (synthetic) | 16.00 |
| | 100.00 |
| C. Compound of Example No. 5 | 10.0 |
| Sodium lignosulfonate | 3.0 |
| Sodium N-methyl-N-oleyl-taurate | 1.0 |
| Kaolinite clay | 86.0 |
| | 100.00 |
| IV. Dusts | |
| A. Compound of Example No. 12 | 2.0 |
| Attapulgite | 98.0 |
| | 100.00 |
| B. Compound of Example No. 9 | 60.0 |
| Montmorillonite | 40.0 |
| | 100.00 |
| C. Compound of Example No. 5 | 30.0 |
| Ethylene glycol | 1.0 |
| Bentonite | 69. |
| | 100.00 |
| D. Compound of Example No. 16 | 1.0 |

-continued

| | Weight Percent |
|---|---|
| Diatomaceous earth | 99.0 |
| | 100.00 |
| V. Granules | |
| A Compound of Example No. 15 | 15.0 |
| Granular attapulgite (20/40 mesh) | 85.0 |
| | 100.00 |
| B. Compound of Example No. 9 | 30.0 |
| Diatomaceous earth (20/40) | 70.0 |
| | 100.00 |
| C. Compound of Example No. 12 | 1.0 |
| Ethylene glycol | 5.0 |
| Methylene blue | 0.1 |
| Pyrophyllite | 93.9 |
| | 100.00 |
| D. Compound of Example No. 10 | 5.0 |
| Pyrophyllite (20/40) | 95.0 |
| | 100.00 |

When operating in accordance with the present invention, effective amounts of the compounds of this invention are applied to the soil containing the seeds, or vegetative propagules or may be incorporated into soil media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages.

The exact amount of active ingredient to be employed is dependent upon various factors, including the plant species and stage of development thereof, the type and condition of soil, the amount of rainfall and the specific compounds employed. In selective pre-emergence application or to the soil, a dosage of from about 0.02 to about 11.2 kg/ha, preferably from about 0.1 to about 5.60 kg/ha, is usually employed. Lower or higher rates may be required in some instances. One skilled in the art can readily determine from this specification, including the above examples, the optimum rate to be applied in any particular case.

The term "soil" is employed in its broadest sense to be inclusive of all conventional "soils" as defined in *Webster's New International Dictionary*, Second Edition, Unabridged (1961). Thus, the term refers to any substance or medium in which vegetation may take root and grow, and includes not only earth but also compost, manure, muck, humus, sand, and the like, adapted to support plant growth.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skills in the art to which the invention pertains.

what is claimed is:

1. A compound represented by the formula

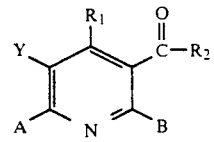

wherein:
A and B are independently selected from fluorinated methyl, chlorofluorinated methyl, and $C_1$–$C_4$ alkoxy, provided that at least one of A and B is trifluoromethyl;
$R_1$ is $C_1$–$C_7$ straight or branched alkyl, cyclopropylmethyl, or $C_3$–$C_6$ cycloalkyl;
$R_2$ is hydroxy, halo, $C_1$–$C_7$ straight or branched alkoxy, or $C_1$–$C_7$ straight or branched alkylthio; and
Y is a radical

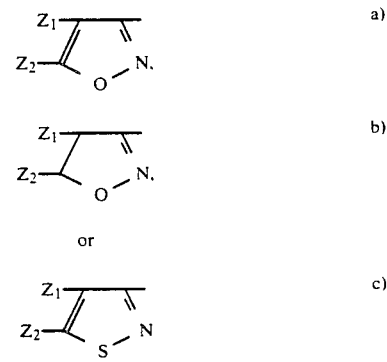

wherein $Z_1$ and $Z_2$ are independently selected from hydrogen, halo, cyano, phenylsulfonyl, $C_1$–$C_6$ straight or branched alkyl, $C_1$–$C_6$ straight or branched alkoxy, and $C_1$–$C_6$ straight or branched alkoxycarbonyl.

2. The compound of claim 1 wherein Y is 3-isoxazolyl.

3. The compound of claim 1 wherein Y is 4,5-dihydro-3-isoxazolyl.

4. The compound of claim 1 wherein Y is 3-isothiazolyl.

5. The compound of claim 2 wherein $Z_1$ is methyl.

6. The compound of claim 5 wherein $Z_2$ is hydrogen.

7. 3-Pyridinecarboxylic acid, 2-(difluoromethyl)-5-(4-methyl-3-isoxazolyl)-4-(2-methylpropyl)-6-(trifluoromethyl)-, methyl ester.

8. A herbicidal composition comprising an adjuvant and an active ingredient of the formula

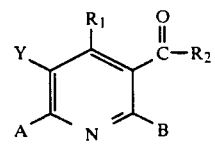

wherein:
A and B are independently selected from fluorinated methyl, chlorofluorinated methyl, and $C_1$–$C_4$ alkoxy, provided that at least one of A and B is trifluoromethyl;
$R_1$ is $C_1$–$C_7$ straight or branched alkyl, cyclopropylmethyl, or $C_3$–$C_6$ cycloalkyl;

$R_2$ is hydroxy, halo, $C_1$-$C_7$ straight or branched alkoxy, or $C_1$-$C_7$ straight or branched alkylthio; and Y is a radical

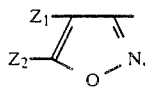  a)

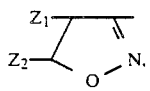  b)

or

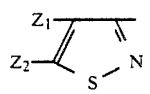  c)

wherein $Z_1$ and $Z_2$ are independently selected from hydrogen, halo, cyano, phenylsulfonyl, $C_1$-$C_6$ straight or branched alkyl, $C_1$-$C_6$ straight or branched alkoxy, and $C_1$-$C_6$ straight or branched alkoxycarbonyl.

9. The composition of claim 8 wherein Y is 3-isoxazolyl.

10. The composition of claim 8 wherein Y is 4,5-dihydro-3-isoxazolyl.

11. The composition of claim 8 wherein Y is 3-isothiazolyl.

12. The composition of claim 10 wherein $Z_1$ is methyl.

13. The composition of claim 12 wherein $Z_2$ is hydrogen.

14. The composition of claim 10 wherein the active ingredient is 3-pyridinecarboxylic acid, 2-(difluoromethyl)-5-(4-methyl-3-isoxazolyl)-4-(2-methylpropyl)-6-(trifluoromethyl)-, methyl ester.

15. A method of controlling undesirable vegetation comprising applying thereto an effective herbicidal amount of a compound represented by the formula

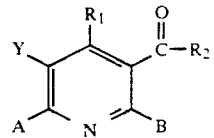

wherein:

A and B are independently selected from fluorinated methyl, chlorofluorinated methyl, and $C_1$-$C_4$ alkoxy, provided that at least one of A and B is trifluoromethyl;

$R_1$ is $C_1$-$C_7$ straight or branched alkyl, cyclopropylmethyl, or $C_3$-$C_6$ cycloalkyl;

$R_2$ is hydroxy, halo, $C_1$-$C_7$ straight or branched or $C_1$-$C_7$ straight or branched alkylthio; and Y is a radical

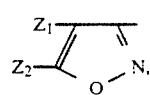  a)

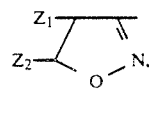  b)

or

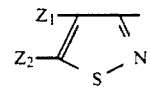  c)

wherein $Z_1$ and $Z_2$ are independently selected from hydrogen, halo, cyano, phenylsulfonyl, $C_1$-$C_6$ straight or branched alkyl, $C_1$-$C_6$ straight or branched alkoxy, and $C_1$-$C_6$ straight or branched alkoxycarbonyl.

16. The method of claim 15 wherein Y is 3-isoxazolyl.

17. The method of claim 15 wherein Y is 4,5-dihydro-3-isoxazolyl.

18. The method of claim 15 wherein Y is 3-isothiazolyl.

19. The method of claim 16 wherein $Z_1$ is methyl.

20. The method of claim 19 wherein $Z_2$ is hydrogen.

21. The method of claim 15, wherein the applied compound is 3-pyridinecarboxylic acid, 2-(difluoromethyl)-5-(4-methyl-3-isoxazolyl)-4-(2-methylpropyl)-6-(trifluoromethyl)-, methyl ester.

* * * * *

UNITED STATES PATENT AND TRADEMARK OFFICE
CERTIFICATE OF CORRECTION

PATENT NO.  : 5,125,961
DATED       : JUNE 30, 1992
INVENTOR(S) : AUINBAUH ET AL.

It is certified that error appears in the above-identified patent and that said Letters Patent is hereby corrected as shown below:

Col. 2, line 64, delete "droisoxazolyl" and insert --dro-isoxazolyl--.

Col. 25, line 65, delete "1 2/3" and insert --1 1/2--.

Signed and Sealed this

Sixth Day of September, 1994

Attest:

BRUCE LEHMAN

Attesting Officer          Commissioner of Patents and Trademarks